United States Patent
André et al.

(10) Patent No.: US 11,660,011 B2
(45) Date of Patent: May 30, 2023

(54) DEVICES AND METHODS FOR SPECKLE MOTION ARTIFACT DETECTION AND COMPENSATION IN MEDICAL IMAGING

(71) Applicant: Stryker European Operations Limited, Carrigtwohill (IE)

(72) Inventors: Marc André, Spiegel (CH); Arthur E. Bailey, North Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 17/138,763

(22) Filed: Dec. 30, 2020

(65) Prior Publication Data
US 2021/0201444 A1   Jul. 1, 2021

Related U.S. Application Data

(60) Provisional application No. 62/955,304, filed on Dec. 30, 2019.

(51) Int. Cl.
| | |
|---|---|
| *G06T 5/50* | (2006.01) |
| *G06T 3/40* | (2006.01) |
| *G06T 7/00* | (2017.01) |
| *G06T 7/20* | (2017.01) |
| *A61B 5/026* | (2006.01) |
| *A61B 5/00* | (2006.01) |

(Continued)

(52) U.S. Cl.
CPC .............. *G06T 3/40* (2013.01); *A61B 5/0261* (2013.01); *A61B 5/7214* (2013.01); *G06T 5/001* (2013.01); *G06T 5/50* (2013.01); *G06T 7/0014* (2013.01); *G06T 7/20* (2013.01); *G06V 10/25* (2022.01); *A61B 2576/00* (2013.01); *G06T 2207/30004* (2013.01); *G06T 2207/30204* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 10,070,796 B2 | 9/2018 | Ostroverkhov et al. | |
| 2003/0120156 A1* | 6/2003 | Forrester | A61B 1/042 600/473 |

(Continued)

FOREIGN PATENT DOCUMENTS

WO      2017176781 A1    10/2017

OTHER PUBLICATIONS

Wijshoff, R.—"On photoplethysmography artifact reduction and applications"—Technische Universiteit Eindhoven 2016, pp. 1-163 (Year: 2016).*

(Continued)

*Primary Examiner* — Bernard Krasnic
(74) *Attorney, Agent, or Firm* — Morrison & Foerster LLP

(57) ABSTRACT

A device for providing reference information in laser speckle medical imaging of tissue of a subject can include a support that includes a marker for image recognition and a speckle target region that is nontransparent to light in a first illumination wavelength range and that generates a speckle pattern when illuminated with light in the first wavelength range. The support can be configured to be attachable to tissue of the subject.

40 Claims, 20 Drawing Sheets
(16 of 20 Drawing Sheet(s) Filed in Color)

(51) Int. Cl.
  *G06T 5/00*   (2006.01)
  *G06V 10/25*  (2022.01)

(56) References Cited

U.S. PATENT DOCUMENTS

2016/0270672 A1    9/2016   Chen et al.
2017/0070692 A1*   3/2017   Lin .................... H04N 5/2176

OTHER PUBLICATIONS

Bozic, I.—"Multi-volumetric registration and mosaicking using swept-source spectrally encoded scanning laser ophthalmoscopy and optical coherence tomography"—SPIE BiOS 2017, pp. 1-6 (Year: 2017).*

Jain, P.—"Measuring light transport properties using speckle patterns as structured illumination"—Scientific Reports—Aug. 2019, pp. 1-10 (Year: 2019).*

Farraro et al., (Sep. 2016). "Handheld, point-of-care laser speckle imaging," Journal of Biomedical Optics 21(9) 094001-1-094001-6.

International Search Report and Written Opinion dated Mar. 8, 2021, directed to International Application No. PCT/CA2020/051807; 6 pages.

Lertsakdadet et al., (2017). "Handheld Laser Speckle Imaging for Point of-Care Blood-Flow Measurements," American Society for Laser Medicine and Surgery Abstracts; 2 pages.

Mahéet al., (2011). "Laser speckle contrast imaging accurately measures blood flow over moving skin surfaces," Microvascular Research 81:183-188.

Omarjee et al., (2015). "Optimisation of movement detection and artifact removal during laser speckle contrast maging," Microvascular Research 97: 75-80.

Richards et al., (Jul. 2014). "Intraoperative laser speckle contrastbrimaging with retrospective motion correction for quantitative assessment of cerebral blood flow," Neurophotonics 1 (1): 015006-1 -015006-11.

* cited by examiner

DEVICES AND METHODS FOR SPECKLE MOTION ARTIFACT DETECTION AND COMPENSATION IN MEDICAL IMAGING

CROSS-REFERENCE TO RELATED APPLICATIONS

This application claims the benefit of U.S. Provisional Application No. 62/955,304, filed Dec. 30, 2019, the entire contents of which are hereby incorporated by reference herein.

FIELD

The present disclosure relates generally to the field of medical imaging, and specifically to medical laser speckle imaging.

BACKGROUND

Laser speckle imaging (LSI) is a promising technique for clinical assessment of tissue perfusion, due to the convenience of the imaging without requiring use of a contrast agent. Tissue perfusion LSI is performed by illuminating a subject tissue area with coherent light and acquiring an image of the laser speckle pattern produced. The speckle pattern signal will fluctuate if there is motion in the subject area, and such fluctuations can be used to detect local motion of blood cells to generate an image of perfusion in the tissue. However, a common issue with the technique is that gross movement of the subject tissue area and/or the LSI device used for imaging introduces errors, or speckle motion artifacts, in the LSI signal, which can make quantitative or comparison applications impractical. The speckle motion artifacts are distinct from blurring or image registration artifacts such as may happen in standard, non-LSI, photography. Because LSI measures motion (blood motion), any motion between the camera and the subject modifies the measured signal. In general, an introduced motion increases the measured LSI signal, with signal change referred to as the speckle motion artifact.

A previous attempt to use a reference patch to provide a measure of the speckle motion artifact in the LSI signal relied on manual designation of the patch location in the acquired images, which may be impractical during routine clinical use and especially if using a handheld LSI device. Furthermore, the previous attempt appeared to teach use of a patch comprising an aluminum layer, which may cause subject discomfort, especially for prolonged patch attachment such as for multiple hours to days for follow-up imaging after clinical treatment.

Other previous work has attempted to reduce speckle motion artifacts in LSI by averaging image frames over several seconds, or by detecting the amount of motion between frames by tracking a fiducial marker on the subject and discarding image frames exceeding a threshold of acceptable motion, but these attempts introduce limitations or discontinuities to the image frame rate that may be undesirable or inadequate in some clinical applications.

Therefore, there is a need for novel and improved modifications to the LSI technique that can facilitate effective and convenient compensation for subject-device motion.

SUMMARY

According to some embodiments, a device may be used to facilitate detection of gross movement between the subject and the imaging device during laser speckle imaging. According to some embodiments, the device can be placed within an imaging field of view, near tissue of interest so that both the device and the tissue of interest are imaged simultaneously. According to some embodiments, the device may include a speckle target region that is nontransparent to illumination light in a wavelength range and that generates a speckle pattern when illuminated with light in that range. The speckle pattern generated by the speckle target region may be representative of gross subject-device motion, and thus, the signal measured in this region can constitute a speckle signal motion value that may be used as a reference value for blood flow or perfusion measurements. According to some embodiments, the device can include one or more markers that may facilitate automated visual recognition of the patch location and orientation within images. Thus, the device according to various embodiments can facilitate effective and convenient compensation for subject-device motion.

According to some embodiments, a device for providing reference information in laser speckle medical imaging of tissue of a subject includes a support that includes a marker for image recognition and further includes a speckle target region that is nontransparent to light in a first illumination wavelength range, and that generates a speckle pattern when illuminated with light in the first wavelength range, wherein the support is configured to be attachable to tissue of the subject.

In any of these embodiments, the support can further includes a window region that is transparent to light in the first wavelength range.

In any of these embodiments, the marker can be detectable under near infrared illumination and not detectable under visible light illumination.

In any of these embodiments, the device can further include a coding region including visually coded information.

In any of these embodiments, the coding region can include a barcode.

In any of these embodiments, the coding region can include a QR code.

In any of these embodiments, the visually encoded information can include a unique identity for the device.

In any of these embodiments, the first wavelength range can be in the near infrared range of the spectrum.

In any of these embodiments, the device can further include multiple material layers, wherein one of the material layers forms the part of the speckle target region that generates the speckle pattern, and another of the material layers forms the part of the speckle target region that is nontransparent to light in the first illumination wavelength range.

According to some embodiments, a method for providing reference information for medical imaging of a subject includes placing a device on the subject, the device comprising a support, wherein the a support comprises at least one marker for automated image recognition and a speckle target region that is nontransparent to light in a first illumination wavelength range and that generates a speckle pattern when illuminated with light in the first wavelength range; illuminating the subject, in a first imaging region including the device, with a light within the first illumination wavelength range; acquiring, with an imaging device, a speckle image of the illuminated imaging region; extracting a speckle signal motion value corresponding to the speckle image signal in the speckle target region; adjusting the speckle image by reference to the speckle signal motion value; and displaying the adjusted speckle image to a user on a display.

In any of these embodiments, adjusting the speckle image signal obtained for the subject can include subtracting the speckle signal motion value from the speckle image signal.

In any of these embodiments, adjusting the speckle image signal obtained for the subject can include normalizing the speckle image signal with respect to the speckle signal motion value.

In any of these embodiments, adjusting the speckle image signal obtained for the subject can include scaling the speckle image signal by a scaling factor and subtracting an offset value, the scaling factor and offset value being based on the speckle signal motion value.

In any of these embodiments, the method can further include acquiring a sequence of speckle images of illuminated imaging regions that overlap the first illuminated imaging region; calculating the relative positions and orientations of the sequence of speckle images based on the relative positions and orientations of the at least one markers; and correcting for relative motion between the imaging device and the subject by aligning the sequence of speckle images based on their relative positions and orientations, through one or more image transformations of translation, rotation, and scaling.

In any of these embodiments, the method can further include extracting a sample speckle image signal from a sample region that is in a fixed, predetermined position relative to the device.

In any of these embodiments, the device can further include a window region that is transparent to light in the first wavelength range, wherein the sample region is within the window region.

In any of these embodiments, the device can further include a coding region including visually coded information.

In any of these embodiments, the coding region can include a barcode.

In any of these embodiments, the coding region can include a QR code.

In any of these embodiments, the visually coded information can include a unique identification for the device.

In any of these embodiments, the first wavelength range can be in the near infrared range of the spectrum.

According to some embodiments, a method of assembling a device for providing reference information in medical imaging, wherein the device is attachable to tissue of an imaging subject, can include providing, on a first layer, a first speckle target region that is nontransparent to light in a first illumination wavelength range; providing, on a second layer, a second speckle target region that generates a speckle pattern when illuminated with light in the first wavelength range; arranging the second layer on top of the first layer, wherein the first speckle target region is aligned with the second speckle target region; and attaching the first layer to the second layer.

In any of these embodiments, can include providing a coding region including visually coded information on the first material layer, the second material layer, or both.

In any of these embodiments, the method can include providing a marker for automated image recognition on the first material layer, the second material layer, or both.

In any of these embodiments, the first speckle target region can absorb at least 90 percent of light intensity in the first illumination wavelength range.

In any of these embodiments, the method can further include providing, on the first material layer, a first window region that is transparent to light in the first wavelength range; and providing, on the second material layer, a second window region that is transparent to light in the first wavelength range, wherein the second window region is located such that it is aligned with the first window region when the first speckle target region is aligned with the second speckle target region.

In any of these embodiments, the first illumination wavelength range can be in the near infrared.

According to some embodiments, a device for providing reference information in medical imaging of a subject can include a support comprising a first speckle target region that absorbs at least 90 percent of light intensity in a first illumination wavelength range and a second speckle target region, aligned with the first, that generates a speckle pattern when illuminated with light in the first wavelength range, wherein the support is configured to be attachable to tissue of the subject.

In any of these embodiments, the support can further include a window region that is transparent to light in the first wavelength range.

In any of these embodiments, the support can further include a marker for automated image recognition.

In any of these embodiments, the marker can be detectable under near infrared illumination and not detectable under visible light illumination.

In any of these embodiments, the support further include a coding region including visually coded information.

In any of these embodiments, the coding region can include a barcode.

In any of these embodiments, the coding region can include a QR code.

In any of these embodiments, the visually coded information can include a unique identity for the device.

In any of these embodiments, the first wavelength range can be in the near infrared range of the spectrum.

In any of these embodiments, the support can include multiple material layers, and wherein a first one of the material layers includes the first speckle target region and a second one of the material layers includes the second speckle target region.

According to some embodiments, a method for compensating for speckle motion artifacts in medical laser speckle imaging of a target tissue area, includes providing a series of laser speckle images of the target, the series of images acquired by a laser speckle imaging device; calculating a measure of relative motion between a first image in the series and a second image in the series; and correcting the image data of the second image to compensate for speckle motion artifacts by scaling the image data by a scaling factor and by subtracting an offset value from the image data, wherein the scaling factor and the offset value are based on the calculated measure of relative motion.

In any of these embodiments, the series of images can include at least 30 images.

In any of these embodiments, the series of images can be acquired during a continuous period of time.

In any of these embodiments, the continuous period of time can be at least 2 seconds.

In any of these embodiments, calculating the measure of relative motion can be based on a measured image signal from any one of devices described above, wherein the device is attached to tissue in the target tissue area.

In any of these embodiments, calculating the measure of relative motion can be based on measurements by a motion sensor mounted to the laser speckle imaging device, the measurements having been acquired simultaneously with the acquisition of the series of images.

In any of these embodiments, calculating the measure of relative motion can be based on calculating, for each image in the series of laser speckle images, a representative value for the laser speckle image signal within a region of interest.

In any of these embodiments, calculating the measure of relative motion can include determining the minimum representative value among the representative values for all images in the series of laser speckle images; and calculating the difference between the representative value for each image in the series of laser speckle images and the minimum representative value; wherein the measure of relative motion for each image in the series of laser speckle images is based on the calculated difference for that image.

In any of these embodiments, the region of interest can include about one quarter of the total number of pixels in each image in the series of laser speckle images, and can include pixels at the center of each image and excludes pixels at the edges of each image.

In any of these embodiments, calculating the measure of relative motion can be based on calculating, for each image in the series of laser speckle images, a first representative value for the laser speckle image signal within a first region of interest and a second representative value within a second region of interest.

In any of these embodiments, calculating the measure of relative motion can include determining a minimum first representative value among the first representative values for all images in the series of laser speckle images; calculating a first difference between the first representative value for each image in the series of laser speckle images and the minimum first representative value; determining the minimum second representative value among the second representative values for all images in the series of laser speckle images; and calculating a second difference between the second representative value for each image in the series of laser speckle images and the minimum second representative value; wherein the measure of relative motion for each image in the series of laser speckle images is based on the calculated first and second differences for an image.

In any of these embodiments, calculating the measure of relative motion can further include calculating an intermediate representative value in an intermediate region of interest between the first and second regions of interest, wherein the intermediate representative value is interpolated based on the first and second representative values; determining the minimum intermediate representative value among the intermediate representative values for all images in the series of laser speckle images; and calculating a third difference between the intermediate representative value for each image in the series of laser speckle images and the minimum intermediate representative value.

In any of these embodiments, each representative value can be a mean value of pixel signal values within the respective region of interest.

In any of these embodiments, each representative value can be a percentile value of pixel signal values within the respective region of interest.

In any of these embodiments, each representative value can be the 20th percentile value of pixel signal values within the respective region of interest.

In any of these embodiments, signal values below a first threshold value can be excluded from the calculation of each representative value.

In any of these embodiments, pixel signal values above a second threshold value can be excluded from the calculation of each representative value.

In any of these embodiments, the method can further include acquiring a second series of laser speckle images of the target, the second series of images acquired by the laser speckle imaging device subsequently to acquisition of the first and second images, wherein correcting the image data of the second image is performed while acquiring the second series of images.

In any of these embodiments, the scaling factor and the offset used for correcting the image data of the second image to compensate for speckle motion artifacts can satisfy the following equations: $SF=1/(1+A \times i)$ and $O=SF \times (B \times i+C)$, wherein SF is the scaling factor, A is a first calibration constant, i is the measure of relative motion for the second image, 0 is the offset, B is a second calibration constant, and C is a third calibration constant.

According to some embodiments, a method for compensating for speckle motion artifacts in medical laser speckle imaging of a target tissue area, includes providing a series of laser speckle images of the target, the series of images acquired by a laser speckle imaging device; calculating a measure of relative motion between a first image in the series and a second image in the series, wherein calculating the measure of relative motion is based on calculating, for each image in the series of laser speckle images, a first representative value for the laser speckle image signal within a first region of interest; and correcting the image data of the second image to compensate for speckle motion artifacts by subtracting an offset value from the image data, wherein the offset value is based on the calculated measure of relative motion.

In any of these embodiments, the series of images can include at least 30 images.

In any of these embodiments, the series of images can be acquired during a continuous period of time.

In any of these embodiments, the continuous period of time can include at least 2 seconds.

In any of these embodiments, calculating the measure of relative motion can include determining the minimum first representative value among the first representative values for all images in the series of laser speckle images; and calculating the difference between the first representative value for each image in the series of laser speckle images and the minimum first representative value; wherein the measure of relative motion for each image in the series of laser speckle images is based on the calculated difference for that image.

In any of these embodiments, the first region of interest can include about one quarter of the total number of pixels in each image in the series of laser speckle images, and can include pixels at the center of each image and excludes pixels at the edges of each image.

In any of these embodiments, calculating the measure of relative motion can be further based on calculating, for each image in the series of laser speckle images, a second representative value for the laser speckle image signal within a second region of interest.

In any of these embodiments, calculating the measure of relative motion can include determining the minimum first representative value among the first representative values for all images in the series of laser speckle images; calculating a first difference between the first representative value for each image in the series of laser speckle images and the minimum first representative value; determining the minimum second representative value among the second representative values for all images in the series of laser speckle images; and calculating a second difference between the second representative value for each image in the series of laser speckle images and the minimum second representative value; wherein the measure of relative motion for each image in the series of laser speckle images is based on the calculated differences for that image.

In any of these embodiments, calculating the measure of relative motion can further include calculating an intermediate representative value in an intermediate region of interest between the first and second regions of interest, wherein the intermediate representative value is interpolated based on the first and second representative values; determining the minimum intermediate representative value among the intermediate representative values for all images in the series of laser speckle images; and calculating a third difference between the intermediate representative value for each image in the series of laser speckle images and the minimum intermediate representative value.

In any of these embodiments, each representative value can be a mean value of pixel signal values within the respective region of interest.

In any of these embodiments, each representative value can be a percentile value of pixel signal values within the respective region of interest.

In any of these embodiments, each representative value can be the 20th percentile value of pixel signal values within the respective region of interest.

In any of these embodiments, pixel signal values below a first threshold value can be excluded from the calculation of each representative value.

In any of these embodiments, pixel signal values above a second threshold value can be excluded from the calculation of each representative value.

In any of these embodiments, the method can further include acquiring a second series of laser speckle images of the target, the second series of images acquired by the laser speckle imaging device subsequently to acquisition of the first and second images, wherein correcting the image data of the second image is performed while acquiring the second series of images.

BRIEF DESCRIPTION OF THE DRAWINGS

The patent or application file contains at least one drawing executed in color. Copies of this patent or patent application publication with color drawings(s) will be provided by the Office upon request and payment of the necessary fee. Features will become apparent to those of ordinary skill in the art by describing in detail exemplary embodiments with reference to the attached drawings in which.

DETAILED DESCRIPTION

Figure 1A:
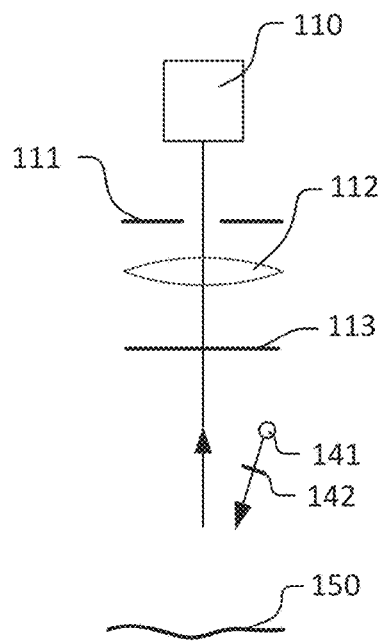
FIGS. 1A and 1B schematically illustrate an optical diagram and a block diagram, respectively, of an exemplary laser speckle imaging (LSI) system.

Reference will now be made in detail to implementations and embodiments of various aspects and variations of the invention, examples of which are illustrated in the accompanying drawings. Although several exemplary variations of the systems and methods are described herein, other variations of the systems and methods may include aspects of the systems and methods described herein combined in any suitable manner having combinations of all or some of the aspects described.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device and/or system for performing the operations herein. This device and/or system may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the processors referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Figure 1B:
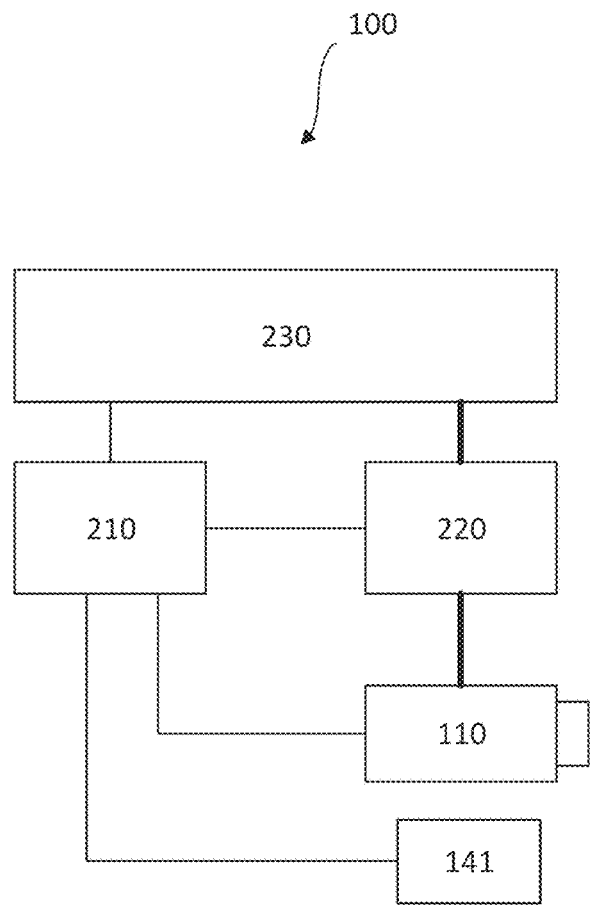

Referring to FIGS. 1A and 1B, shown there is a laser speckle imaging system 100 which may be used, for example, to image tissue perfusion. The imaging system 100 may comprise a coherent light source 141 for illuminating tissue 150 of a subject, an image sensor 110 comprising optical components, a control unit 210, a processing unit 220, and a user interface 230 (e.g., a human-machine-interface "HMI"). In some variations, the coherent light source 141 may include a single mode laser source at about 800 nm+/−about 50 nm. At this wavelength, the absorption for oxy- and deoxyhaemoglobin is substantially equal. It should be appreciated that the coherent light source need not be limited to this wavelength, as long as the image sensor is sensitive to the illumination wavelength.

Optics 142 such as, for example, an engineered diffuser and/or lens system, may be used to shape or otherwise modify illumination of a region on the tissue 150. In some variations, the image sensor 110 may be a CMOS or CCD type color image sensor and may acquire light from the illuminated part of the object or region of interest through a lens or objective 112. In some variations, the image sensor 110 may be a CMOS or CCD type grayscale image sensor. A filter 113 (e.g., a long-pass or band-pass filter) may be used to filter light so as to only acquire the wavelength of the coherent illumination source. In the variation shown in FIG. 1, an aperture 111 may be used to adjust the speckle size on the image sensor 110. The speckle size may be adjusted to optimize the speckle contrast on the image sensor 110.

The control unit 210 may control the image acquisition, and in some variations, may pulse coherent light from the coherent light source 141 (e.g., laser). In some variations, the control unit 210 may control or adjust the exposure time of the image sensor 110. The exposure time should be sufficiently long such that the moving speckle pattern blurs the speckle image, but short enough such that the expected moving speeds can be differentiated. In some variations, the exposure time may be in the range of about 1 ms to about 10 ms. In some variations, the exposure time is at least 1 ms, at least 2 ms, at least 3 ms. In some variations, the exposure time is less than 20 ms, less than 10 ms, less than 8 ms. These exposure times may be desirable for measuring the perfusion in human skin. Furthermore, the exposure time may be fixed or adjustable depending on the object or region of interest.

The acquired speckle images may be transferred to the processing unit 220, which may calculate the perfusion images. In some variations, the calculation process may include calculating a contrast image and converting the contrast image to a perfusion image. The contrast image is calculated by dividing the mean pixel values by the standard deviation of the pixel values in a small area (kernel) of the image. The kernel size may be, for example, 7×7 to 15×15 pixels. The process is calculated for many kernels in the image. Generally, the contrast image may be converted to a perfusion image by relying on an inversely proportional relationship between the square of the speckle contrast and the flow parameters (e.g., speed, concentration, etc.) of particles (e.g., red blood cells in capillaries). One skilled in the art will appreciate that the systems, devices, and methods described herein shall not be limited to the details of the processing algorithm.

In some embodiments the processing algorithm is used as follows: Speckle contrast (K) is defined in terms of the standard deviation ($\sigma_s$) and the mean speckle intensity fluctuations $\langle I \rangle$. While the contrast and mean intensity could also be determined in time-domain, the processing in spatial-domain has advantages in reducing motion artefacts. The relation between speckle contrast and spatial variance of the time-averaged speckle pattern is:

$$K = \frac{\sigma_s}{\langle I \rangle} = \sqrt{\int_0^T |g(\tau)|^2 \frac{d\tau}{T}}$$

where $g(\tau)$ is the normalized autocorrelation function, $\tau$ is the lag time, and T is the camera exposure time. The exposure time is often selected in the range of 1-10 ms. Assuming a Lorentzian spectrum the relationship can be rewritten as:

$$K = \sqrt{\frac{\tau_c}{2T}\left(1 - e^{\frac{-2T}{\tau_c}}\right)}$$

where $\tau_c$ is the correlation time and $$\frac{T}{\tau_c}$$

is proportional to the mean velocity V. This can be further approximated to:

$$V = \frac{T}{\tau_c} \approx \frac{1}{K^2}$$

While V has a linear response to velocity within the assumed range limited by the exposure time, it also depends on the concentration of the moving scatterers vs. the static scatterers (i.e. the concentration of blood). Thus V is often also referred as LSI value, flow or perfusion.

The perfusion image may be shown on the user interface 230. The user interface 230 may include, for example, a display and input means such as mouse, keyboard, buttons, or touch screen. In some variations, the sequence of some or all of the optics elements such as the aperture 111, the lens 112, the filter 113, or a combination thereof may be rearranged.

Speckle Motion Artifact Detection

An adhesive patch may be used to provide reference information during laser speckle imaging, and may facilitate detection of gross movement between the subject and the imaging device. The patch may also facilitate image registration between successive image frames in one session, or between images from separate imaging sessions, by serving as a highly visible fiducial marker. The patch may be placed within the imaging field of view and near to the tissue of interest, so that both may be imaged simultaneously. The size of the patch may be any size that is appropriate for a particular application such that the patch is large enough to be reliably imaged but not so large that it obscures imaging of the tissue of interest.

Figure 2:
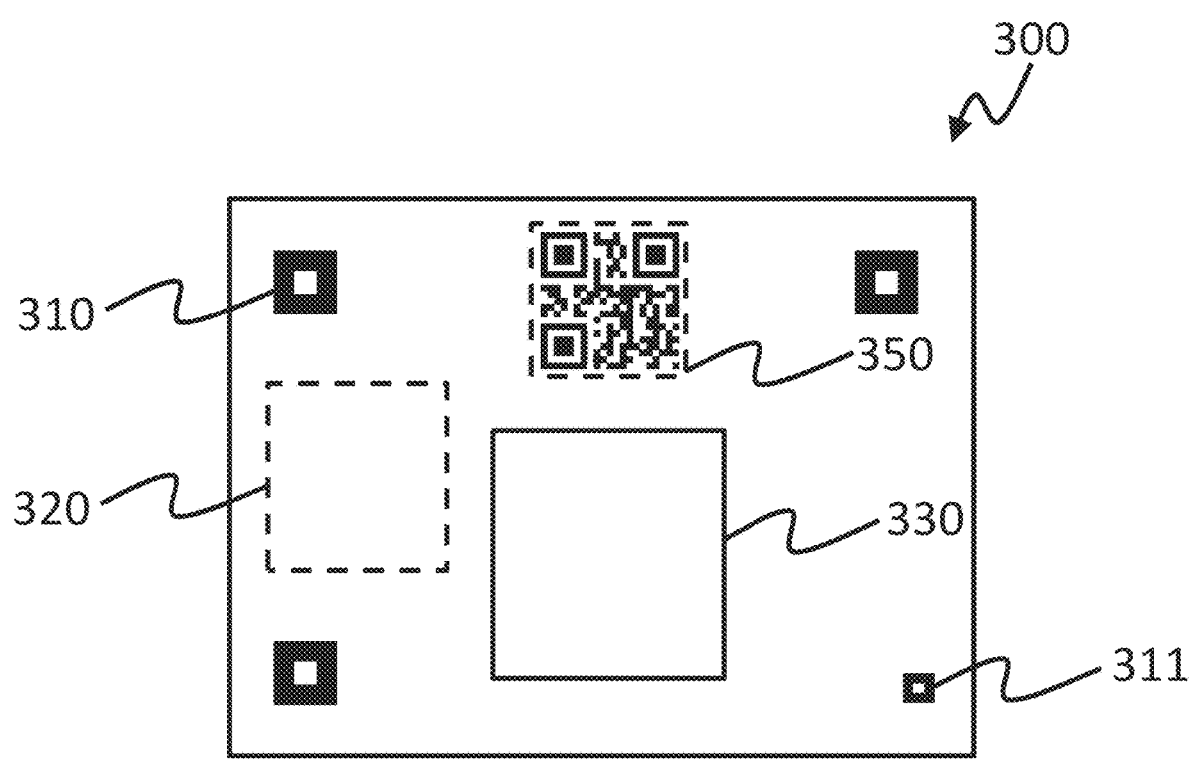
FIG. 2 is an illustrative diagram of an adhesive patch according to an embodiment.

FIG. 2 depicts several features of an exemplary embodiment of an adhesive patch 300. The patch 300 may feature one or more markers 310 which may facilitate automated visual recognition of the patch location and orientation within images acquired with an imaging device. Markers 310 may be of any size and shape that may be reliably resolved by the imaging device. A plurality of markers 310 of a known size and shape may be arranged in a known pattern on the area of the patch 300, such as, for example, in multiple corners of the patch. One or more markers 311 of a second known size and shape may also be arranged as part of the known pattern on the patch 300, to assist with recognition of the orientation of the patch. Markers 310 and or markers 311 may also facilitate image registration between frames. In some variations, the markers may be detectable under near infrared illumination, for example in case the imaging device is configured for near infrared imaging. In some variations, the markers may be detectable under illumination with wavelengths in the range of about 750 to 850 nm. In some variations, the markers may be detectable under near infrared illumination, but not detectable under visible light illumination, for example to prevent the markers from being a distraction to the user when viewing the subject and patch directly or when viewing visible light images of the subject.

A portion of the patch 300 may comprise a speckle target region 320 that is nontransparent to illumination light from an imaging device in a first wavelength range and that generates a speckle pattern when illuminated with light in that range. In some embodiments, the first wavelength range may be in the near infrared. In some variations, the first wavelength range may be about 750 to 850 nm. Because the fixed adhesive patch does not feature any moving parts, the only motion that the laser speckle signal corresponding to the speckle target region 320 will be representative of is gross subject-device motion, and thus the signal measured in this region can constitute a speckle signal motion value that may be used as a reference value for blood flow or perfusion measurements. For example, the laser speckle signal of an image acquired by the imaging device may be adjusted by reference to the laser speckle signal of the speckle target region 320, the speckle signal motion value, such as by subtracting the speckle signal motion value and/or by normalizing the speckle image signal with respect to the speckle signal motion value. In some embodiments, the speckle target region 320 may comprise multiple unconnected areas on the patch 300.

A portion of the patch 300 may comprise a data region 350 that may contain encoded data. For example, data region 350 may contain visually encoded data such as a barcode or a QR code. In some variations, the visually encoded data in data region 350 may be visible when illuminated by light in the visible wavelength range and/or by light in the near infrared range. In some variations, the visually encoded data in data region 350 may be visible when illuminated by light in the near infrared range, and not visible when illuminated by light in the visible wavelength range.

The patch may also contain Near Field Communication (NFC) means, such as RFID, and data storage capability for NFC data. The NFC data may contain the same or different data as the data region 350 or it may replace the data region.

A portion of the patch 300 may comprise a skin reference region 330 which may provide a window region through which to obtain a reference measure of the LSI signal for comparison with measures of the LSI signal in other subject areas of interest. In some embodiments, a skin reference region 330 may be formed by a cutout or hole formed in a region of the patch 300. In some embodiments, a skin reference region 330 may be formed by a material that is transparent to light in the first wavelength range. In some variations, a region that is outside of the boundaries of the patch 300 and that is located at a predetermined location relative to the patch 300 may be used as a skin reference region.

The skin reference region 330 may be used for indicating a consistent reference zone for intra-individual relative imaging such as the intra-individual relative imaging disclosed in WO/2013/160861.

Figure 3:
FIG. 3 is an illustrative diagram of a side profile of an adhesive patch according to an embodiment.

In some embodiments, an adhesive patch for use with laser speckle imaging may comprise multiple material layers. For example, FIG. 3 depicts an exemplary embodiment of a patch 400 comprising a speckle generating layer 420 and an illumination blocking layer 440. The speckle generating layer 420 may comprise any material that generates a speckle pattern when illuminated with light in the first wavelength range. For example, in some embodiments a white paper label may be used as a speckle generating layer 420. The illumination blocking layer 440 may be any material that blocks illumination light in the first wavelength range from reaching or penetrating the skin. For example, the illumination blocking layer 440 may block between 99 to 100 percent, between 95 to 100 percent, or between 90 to 100 percent of the illumination light intensity in the first wavelength range. In some variations, the illumination blocking layer may block at least 80 percent, at least 90 percent, at least 95 percent of the illumination light intensity in the first wavelength range. In some variations, the illumination blocking layer may block 100 percent, at least 99 percent, at least 98 percent of the illumination light intensity in the first wavelength range. The blocking layer 440 may be comprised of an absorptive material or a reflective material with respect to the first wavelength range, or a combination of absorptive and reflective materials. For example, in some embodiments an absorptive black masking tape such as Thorlabs T743-1.0 may be used as an absorptive material to comprise blocking layer 440. Reflective materials may be used to block the illumination light from reaching or penetrating the skin, including metals such as aluminum, silver, or gold. However, use of a reflective material may result in image artifacts if some of the reflected light contributes to images acquired by the imaging device.

In some embodiments, a patch 400 may be partially constructed and/or manufactured at or before the time of use by combining a speckle generating layer 420 with an illumination blocking layer 440. For example, an illumination blocking layer 440 may be placed on a subject and then a speckle generating layer 420 may be placed on the illumination blocking layer 440 to form a patch 400. As another example, a speckle generating layer 420 may be placed on an illumination blocking layer 440 to form a patch 400, and then the patch may be placed on a subject. In some variations, the illumination blocking layer 440 may have two adhesive surfaces. In some variations, the illumination blocking layer 440 may have an adhesive surface and the speckle generating layer 420 may have an adhesive surface.

In some embodiments, an adhesive patch may include an adhesive that is suitable and biocompatible for multiple days of use, such as is used in typical dermal or transdermal patches, so that the patch may be used in one or more follow-up imaging sessions after an initial imaging session. For example, the patch may be used to assist with imaging and perfusion assessment during a surgical session such as a surgery involving a skin flap, and may also be used during imaging in one or more post-operative follow-up sessions tracking progress of the skin flap and surrounding tissue. Use of the same patch for multiple imaging sessions may facilitate precise image registration and/or alignment between images obtained in separate sessions, by using the patch as a clearly visible fiducial marker. Use of the same patch may also facilitate automatic recognition of the subject identity and the subject's imaging history and other notes associated with the subject and triggering instructions in the image processor, including, for example, automatically loading the same imaging settings as used in a previous imaging session, and recording images to the same imaging history as used in a previous imaging session. Such automatic recognition and triggering of image processor instructions may be facilitated by recognition of a unique patch identification that may be stored in the patch data region 350.

In some variations the unique patch identification is a serial number. In yet another variation the unique patch identification is a numerical or alpha-numerical code which is unique and encoded in such a way that every code can only be generated with specific know-how (e.g. by use of a symmetrical or asymmetrical encryption or signature). Such unique patch identification could be used as payment confirmation for a pay-per-use model.

One or more other techniques of speckle motion artifact detection may be used alternatively to, or in combination with, use of an adhesive patch for such detection. For example, image processing may be performed to process multiple image frames, calculate a measure of relative motion (e.g. motion between the camera and the subject) occurring between image frames, and estimate the speckle motion artifacts due to such motion. As a further example, motion sensors such as accelerometers and/or gyroscopes may be used to measure motion parameters of the imaging device and to estimate the speckle motion artifacts due to such motion.

Figure 4:
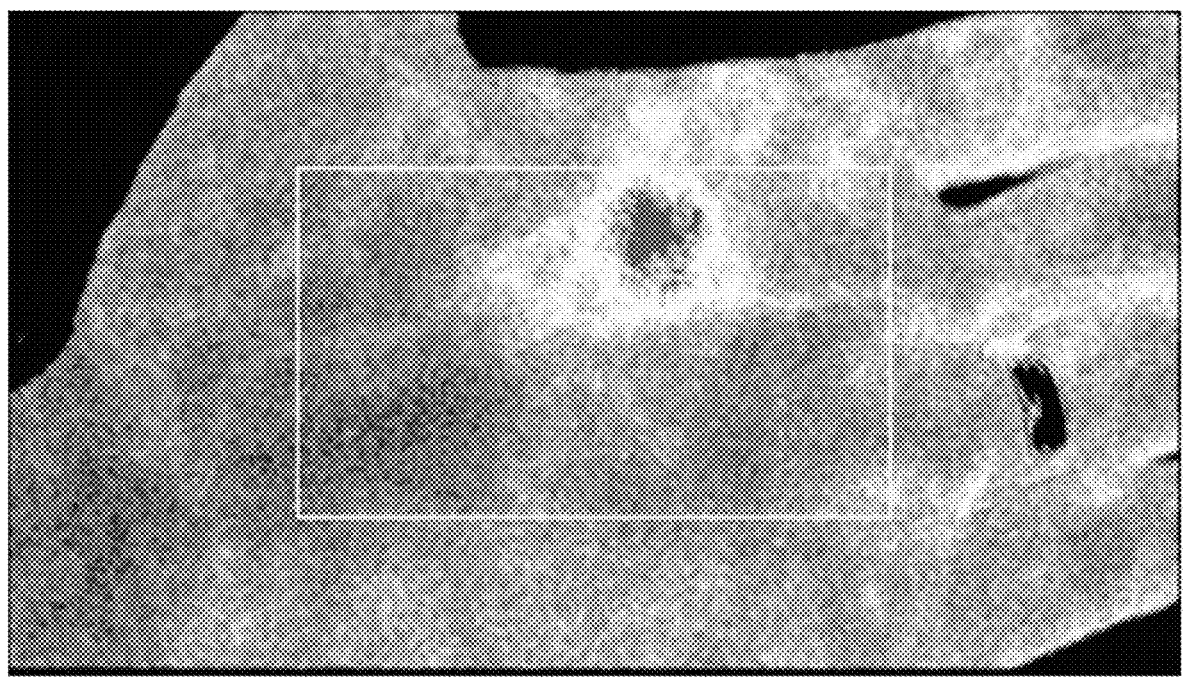
FIG. 4 shows a sample LSI image with a region of interest (ROI) illustrated according to an embodiment.

In some embodiments, a measure of relative subject-device motion between image frames may be based on calculation of representative values within a region of interest (ROI) in the images. FIG. 4 shows an example of a region of interest overlaid on a sample LSI image. In the non-limiting example depicted, the ROI covers about one quarter of the image area and includes pixels at the center of each image and excludes pixels at the edges of each image.

In some embodiments, in order to calculate a measure of relative subject-device motion between images in a series of images, a representative value may be calculated for each image in the series and the minimum representative value among the representative values for all images in the series may be determined. The difference between the representative value for each image in the series and the minimum representative value may then be calculated and used as the basis for the measure of relative subject-device motion for each image. In some embodiments, the number of images included in the series of images for these calculations may represent 1, 2 or 3 seconds of image acquisition (with a frame rate of 30 fps, this corresponds to at least about 30, at least about 60, or at least about 90 images). In some variations the frame rate may be 60 fps or 120 fps.

Figure 8:
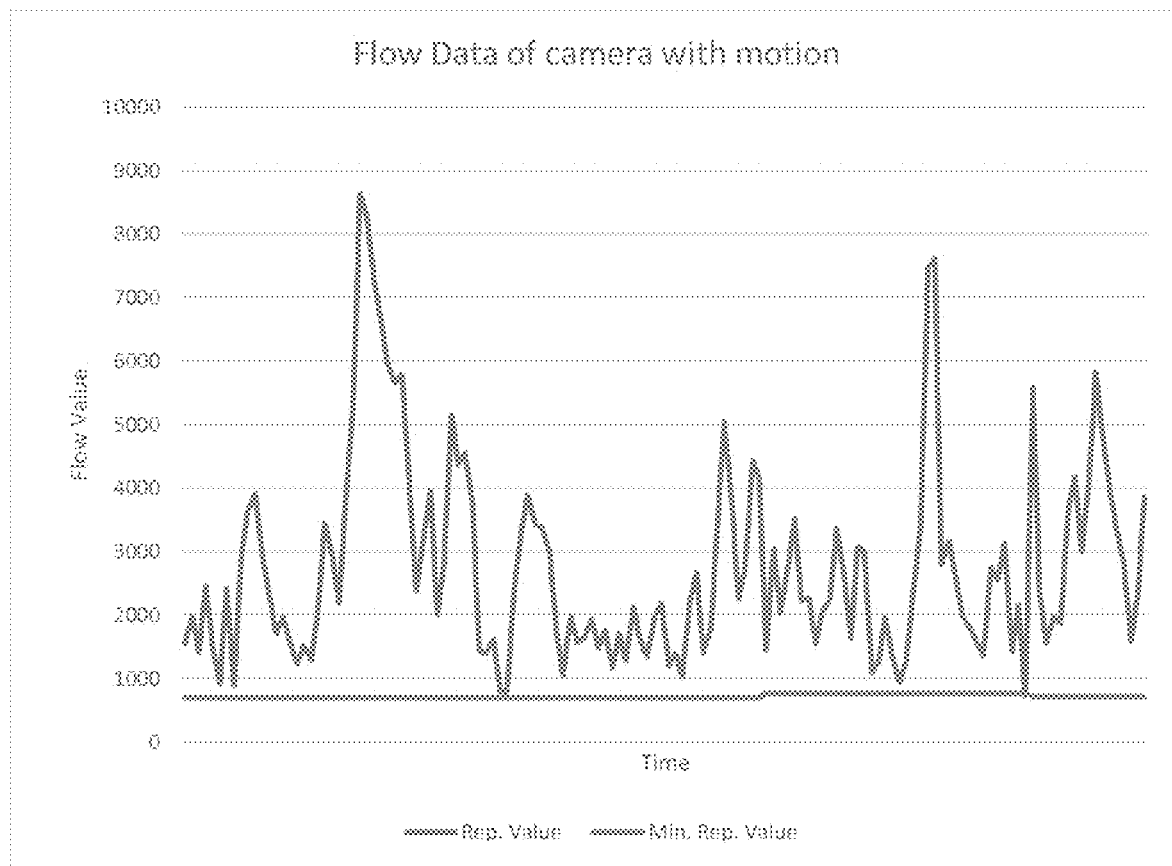
FIG. 8 shows an example of a time-domain graph of the representative value in a test-bench setup.

If it can be assumed that the operator tries to keep the camera stable, at least one frame in the series of images is typically quite stable, thus the difference between the representative values allows determining the LSI value without motion, or with minimal motion, for at least one frame. This information can then be used to approximate the motion for any other frame by comparing representative values. One example is given in FIG. 8, which shows a time-domain graph of the representative value in a test-bench setup. The representative value is very volatile from frame to frame in the handheld camera in this example, but the minimum representative value remains quite stable. The minimum representative value therefore corresponds well to the LSI value without introduced motion.

In some embodiments, the calculation of a representative value within a ROI may be performed on each acquired single image frame in order to have the highest possible temporal resolution for characterizing a measure of relative subject-device motion, while one or more single image frames may subsequently be averaged for display.

Figure 5A:
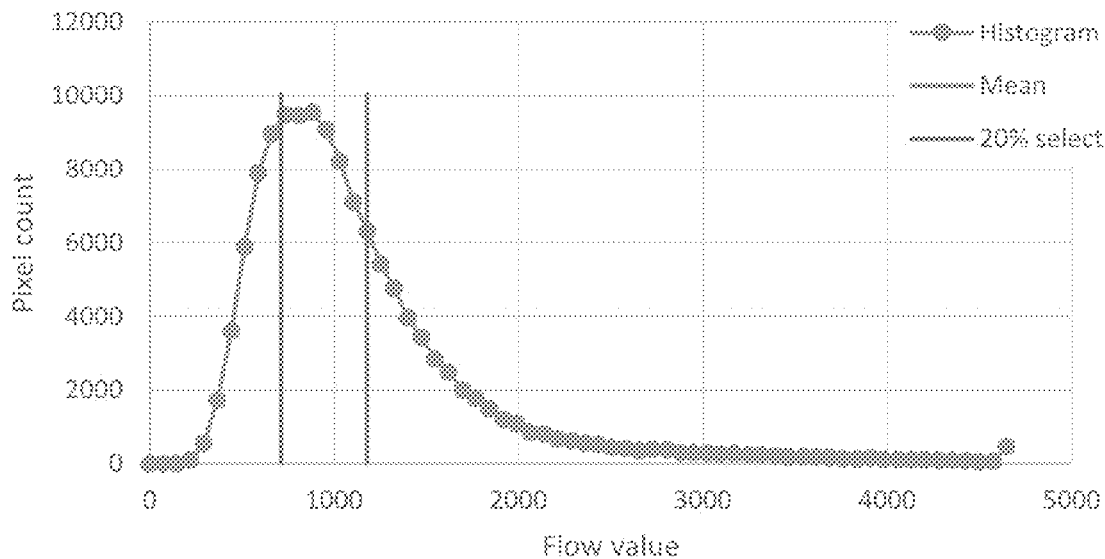
FIGS. 5A and 5B show sample histograms of LSI images and illustrate the corresponding mean value and 20th percentile value.
Figure 5B:
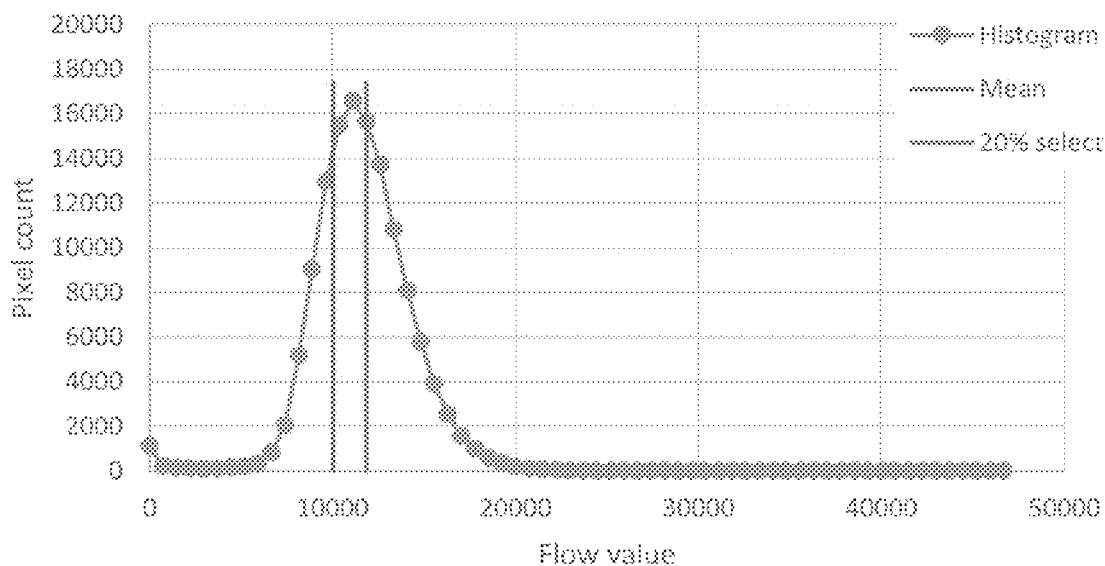

In some embodiments, the representative value may be chosen to yield a value of the baseline perfusion in the ROI. For example, a percentile value, mode, mean, or any other statistic with regard to the distribution of LSI values for the pixels within the ROI may be used. With regard to a typical histogram of such a distribution of LSI values, such as displayed in FIG. 5A, it may be noted that the distribution is often skewed right with the mean value higher than the median. In such cases, it may be useful to use a value lower than the mean as the representative value, because the mean may be influenced more by speckle motion artifacts increasing the LSI values. For example, it may be useful to use a percentile value of the LSI values for the pixels within the ROI as the representative value. FIGS. 5A and 5B show examples of a $20^{th}$ percentile value being selected. As a further example, the mode value of the distribution LSI values for the pixels within the ROI may be used as the representative value. In FIGS. 5A and 5B the mode value is represented as the peak value on the histogram curve. In some variations, the representative value may be based on a measure of the width of the distribution of LSI values, such as the Full Width at Half Maximum.

In some embodiments, it may be useful to exclude some pixels in the ROI from the calculation of the representative value, in order to better represent the baseline perfusion in the ROI. For example, pixel values below a first threshold value may be excluded from calculation of the representative value. For example, the pixel values before the first threshold value may include pixel values at or near zero and/or other relatively low pixel values. Additionally or alternatively, pixel values above a second threshold value may be excluded from calculation of the representative value. For example, the pixel values above the second threshold value may include saturated pixel vales and/or other relatively high pixel values.

In one example the representative value may be calculated as the $20^{th}$ percentile value of the LSI value V within a centered ROI that covers ¼ of the total image before any time-domain filtering is performed. In other examples the representative value may be calculated as other percentile values, for example, the $25^{th}$ percentile value of the LSI value V within a centered ROI that covers ¼ of the total image before any time-domain filtering is performed.

In some embodiments, multiple ROIs may be specified within each image, and a measure of relative subject-device motion may be calculated for each ROI, so that different relative motion in different parts of the image may be separately corrected for. Instead of calculating a single representative value for each image as described above, representative values may be calculated for each ROI within the image. After calculating the representative values in the multiple ROIs, one or more intermediate representative values may be calculated in one or more intermediate ROIs between the multiple ROIs by interpolation based on the representative values in the multiple ROIs and the relative positions of the multiple ROIs and the one or more intermediate ROIs.

In some embodiments the series of images may be first registered to align showing the same target area before the calculation of relative motion is performed. Registration methods are known to those skilled in the art. The registration may be based on feature detection, patch detection or motion/gyro sensors.

In case a user of a handheld laser speckle imaging device wishes to save an image of subject tissue near to a particular time point while imaging, the best candidate image for saving may be selected automatically from a series of recently acquired images based on a measure of motion or speckle motion artifacts, such as any of the measures described herein, so as to select the candidate image suffering from the smallest amount of speckle motion artifacts. Such a method for automatically selecting the best candidate image may be implemented without, or in combination with, methods of speckle motion artifact compensation on the series of acquired images, such as any of the methods of speckle motion artifact compensation described herein. In some embodiments, one or more of the images in the series of recently acquired images may be calculated from an average of a number of nearby images, in order to reduce speckle motion artifacts and/or noise.

Figure 6:
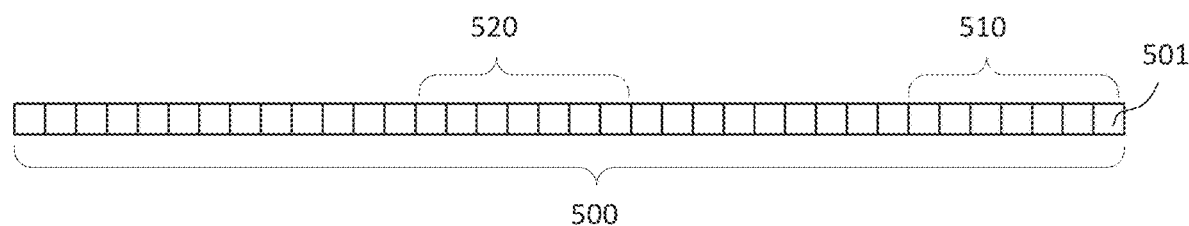
FIG. 6 shows a diagram of an embodiment of an image frame buffer used for automatic candidate image selection and saving.

FIG. 6 shows an image frame buffer 500 used for automatic candidate image selection and saving, according to an embodiment. Image frame buffer 500 includes a series of recently acquired images up to the most recent image frame 501. The collection of image frames 510 represents a conventional selection of image frames up to the most recent image frame 501, selected without regard to any measure of motion or speckle motion artifacts present during acquisition of the image frames within image frame buffer 500. In contrast, the motion optimized collection of image frames 520 represents an optimized selection of image frames that may be automatically selected, from any part of image frame buffer 500, based on the motion or speckle motion artifacts detected during acquisition of the image frames within the image frame buffer 500. The motion optimized collection of image frames 520 may be comprised of any number of one or more image frames, and the one or more image frames may be averaged to provide the candidate image for saving. In some embodiments, the measure of speckle motion artifacts in the image frames in image frame buffer 500 may be the measured perfusion signal, for example if assuming that the minimum measured perfusion signal represents the signal with the least motion and the least corresponding speckle motion artifact artificially increasing the measured perfusion signal.

In one embodiment the selection of the motion optimized frames 520 is done by calculating the mean representative value for any sequence of N consecutive frames and selecting the sequence of N consecutive frames which has the mean representative value. The candidate image for saving is then calculated as the pixel-by-pixel time-domain averaged image of the selected N consecutive frames. The choice of N may be made depending on the frame-rate. For 30 fps, it may be chosen in the range of 1 to 30 frames, for example.

Speckle Motion Artifact Compensation

One or more of the methods and systems described herein for calculating a measure of relative subject-device motion between laser speckle images may be combined with a method of speckle motion artifact compensation in order to compensate for speckle motion artifacts in the images.

Use of an adhesive patch such as any of those described herein may permit correction for speckle motion artifacts in the laser speckle image signal, because the adhesive patch may provide an image signal region that is purely due to motion between the imaging device and the subject surface. In some embodiments, it may be assumed that the measured LSI signal over regions with exposed subject skin includes a sum of a first LSI signal due to motion of blood cells in perfused tissue beneath the skin and a second LSI signal due to motion between the imaging device and the subject skin. It may also be assumed that the measured LSI signal over a speckle target region on an adhesive patch is primarily composed of only the LSI signal due to motion between the imaging device and the subject skin. Therefore, to compensate for speckle motion artifacts that may distract from the blood cell LSI signal of interest, the measured LSI signal over a speckle target region on an adhesive patch may be subtracted from the entire LSI signal. In some embodiments, if a material is used on the exposed surface of the target speckle region of the patch that results in a different signal contribution from gross subject-device motion than would be measured on subject tissue, then calibration may be performed in order to determine an appropriate calibration factor to scale the target speckle region signal before subtracting the calibrated result from the subject tissue signal. For example, calibration may be performed by placing a patch in the same imaging field of view as a tissue region known to be free of any perfusion or blood flow, such as a cadaver specimen, and measuring the LSI signal on the target speckle region of the patch and in the tissue region during subject-device motion.

Output from one or more of the methods described herein for calculating a measure of relative subject-device motion between image frames may also be used to compensate for speckle motion artifacts by subtracting an offset value from the image data of each image, with the offset value being based on the calculated measure of motion for each image. For example, the offset value may represent an estimate of the LSI signal due to subject-device motion.

Additionally or alternatively to subtracting an estimate of the LSI signal due to motion from the measured LSI signal to correct for speckle motion artifacts, other operations may be performed on the measured LSI signal based on a measure of relative subject-device motion between laser speckle images to correct for speckle motion artifacts. For example, in some applications it may be observed that speckle motion artifacts result in a scaling of laser speckle image data in combination with subtracting an offset from the laser speckle image data, and in these cases correction of the laser speckle image data may be performed by scaling the image data by a scaling factor and by subtracting an offset value from the image data based on a calculated measure of relative subject-device motion.

Figure 7:
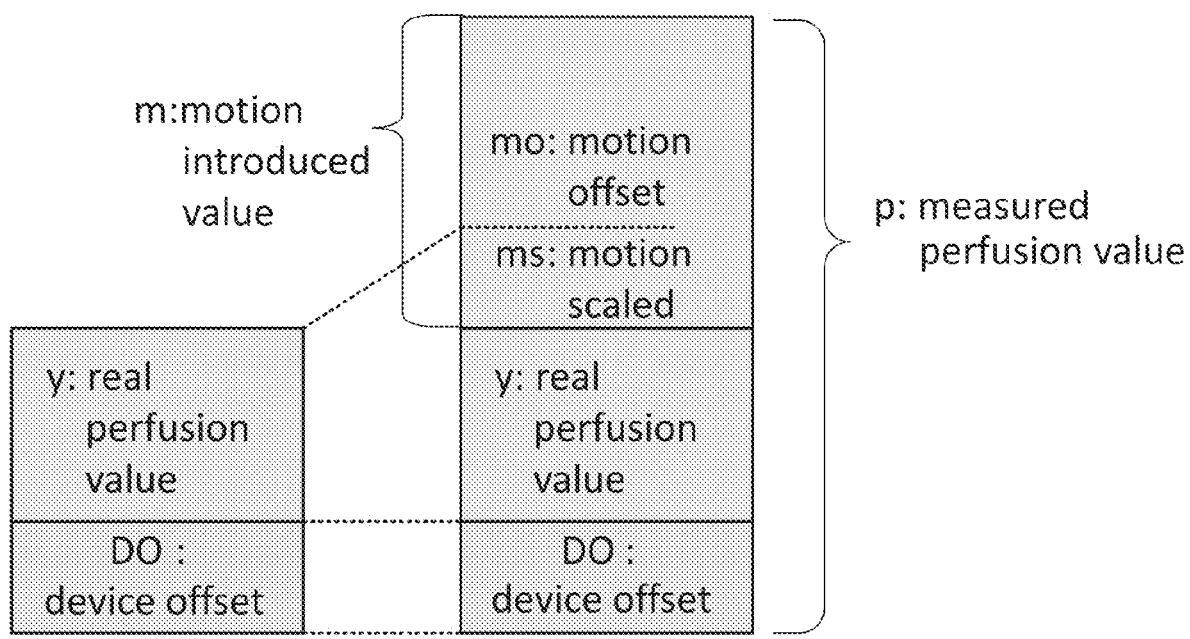
FIG. 7 depicts a model of the components contributing to a measured perfusion value as displayed in a laser speckle image, according to an embodiment.

FIG. 7 depicts a model of the components contributing to a measured perfusion value as displayed in a laser speckle image, according to an embodiment. The model shows that in a stable case the measured perfusion (p) is the sum of the true perfusion value (y), which represents the clinically significant component, and a device calibration value (device offset, DO). When a motion between the camera and subject is introduced, the measured perfusion (p) consists of the sum of real value (y), the device offset (DO) and the motion introduced value (m). The latter consists of two components, a motion related scaled component (ms) and a motion related offset (mo). The motion related scaled component (ms) depends on the motion and the true perfusion value (y) and is a scaling of the true perfusion value. The motion related offset (mo) only depends on the motion and is independent of the true perfusion value (y). The device offset (DO) represents a fixed calibration offset.

For example, the following equations demonstrate how a scaling factor (SF), and offset (O) value may be calculated for a given measure of relative subject-device motion (i). The speckle motion artifact (m), in the image may be assumed to be comprised of a motion offset component (mo), and a motion scaled component (ms), which are equivalent to a function of the true perfusion value (y) multiplied by the measure of relative subject-device motion (i).

$$m = mo + ms = f(y) \cdot i$$

The true perfusion value (y), may be calculated from the measured perfusion value (p), by subtracting the device offset and the speckle motion artifact.

$$y = p - DO - m = p - DO - f(y) \cdot i$$

f(y) may be approximated as a linear function.

$$f(y) = Ay + B$$

Then, the real perfusion value (y) may be rewritten as:

$$y = \frac{p}{1 + A \cdot i} - \frac{B \cdot i + DO}{1 + A \cdot i}$$

The scaling factor (SF) may be calculated as:

$$SF = \frac{1}{1 + A \cdot i}$$

The offset (O) to be subtracted may be calculated as:

$$O = SF \cdot (B \cdot i + DO)$$

The constant parameters A, B and DO may be experimentally calibrated. DO may be determined, for example by measuring the perfusion value in a very stable setup and imaging a completely static target without any perfusion. DO may be taken as the lowest response that the system can measure, and it largely depends on the optical setup and the image sensor noise. A and B may be tuned such that in an image that has both high and low perfused regions, both the high and low perfused regions are stable despite introduced motion. Images may be acquired in stable and motion-introduced conditions. All those images may be processed to calculate the real perfusion value (y). A and B can be tuned so that both high and low perfused regions keep their real perfusion value in all those images. In one approach B may be calibrated first and A may then be used to further tune the correction. In some embodiments, for example, A may be set to around 0.00016, B may be set to around 0.78, and DO may be set to around 150.

Considering that the scaling factor (SF) and offset (O) are each functions of the measure of motion (i), the motion corrected perfusion (y) for any given frame can then be calculated from the measured perfusion (p) as:

$$y=SF(i)\cdot p-O(i)$$

The measure of motion (i) may be determined in different ways as described in this invention. If the motion is determined by finding the minimum representative value, the measure of motion (i) is the difference between the representative value of the current frame ($r_a$) and the minimum representative value ($r_m$). In that case the measure of motion (i) is calculated as:

$$i=(r_a-r_m)$$

The example above should not limit the exact way of how the motion compensation is performed. In a generic approach, the real value (y) is a function of the measured perfusion (p) and the measure of motion (i).

$$y=f(p,i)$$

In some embodiments, any combination of one or more of the methods described herein for calculating a measure of relative subject-device motion and correcting image data to compensate for speckle motion artifacts may be performed in real time. For example, in some variations a subsequent second series of images may be acquired by the laser speckle imaging device while calculations for correcting the image data from a first series of images are being performed. As another example, in some variations after performing calculations for correcting the image data from a series of images the series may be modified by removing one or more images from the series and acquiring one or more new images, adding the new images to the modified series, and then correcting the modified series of images. In such real time image correction embodiments, some computational effort may be saved by reusing representative values already calculated for any image frames that are carried forward from a first series of images to a second or to a modified series of images.

In some embodiments, any combination of one or more of the methods described herein for calculating a measure of relative subject-device motion and correcting image data to compensate for speckle motion artifacts may be performed in post-processing after a sequence of images has been acquired and saved.

In some embodiments, any combination of one or more of the methods described herein for calculating a measure of relative subject-device motion and correcting image data to compensate for speckle motion artifacts may be performed to correct the image data on a pixel by pixel basis for each pixel in the image data.

In some embodiments, any combination of one or more of the methods described herein for calculating a measure of relative subject-device motion and correcting image data to compensate for speckle motion artifacts may be performed to correct a subset of pixels within the image data.

In some embodiments the image data may be registered to compensate for any displacement that accrued due to motion. Registration methods are known to those skilled in the art. The registration can be based on feature detection, patch detection or motion/gyro sensors.

The methods, embodiments, and systems described herein may be used for blood flow imaging, tissue perfusion imaging, or a combination thereof, which may be performed during an invasive surgical procedure, a minimally invasive surgical procedure, a non-invasive surgical procedure, a non-invasive and non-surgical clinical procedure and/or assessment, or a combination thereof. Examples of invasive surgical procedures which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. An example of a non-invasive and non-surgical clinical assessment includes wound assessment, for example to assist with perfusion imaging in and around the wound to facilitate ascertaining what course of treatment may or may not be required.

It will be appreciated that any options mentioned in view of any of the methods, embodiments, and systems may be used in conjunction with the other methods, embodiments, and systems, and vice versa. It will be appreciated that any of the options may be combined. It will be appreciated that any of the aspects may be combined. It will be appreciated that any of the embodiments and/or variations may be combined with the methods, embodiments, and systems described herein.

EXAMPLES

Figure 9A:
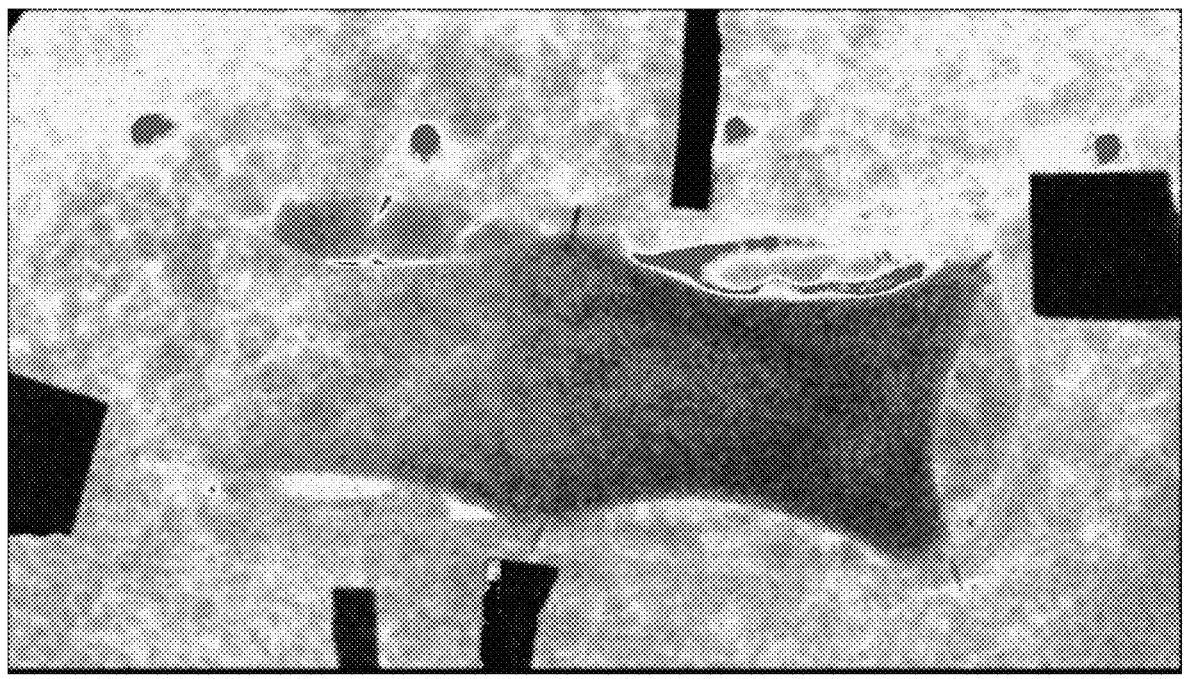
FIGS. 9A and 9B show sample uncorrected laser speckle images and images corrected for speckle motion artifact, respectively, obtained with the imaging device mounted in a fixed position relative to the subject.
Figure 9B:
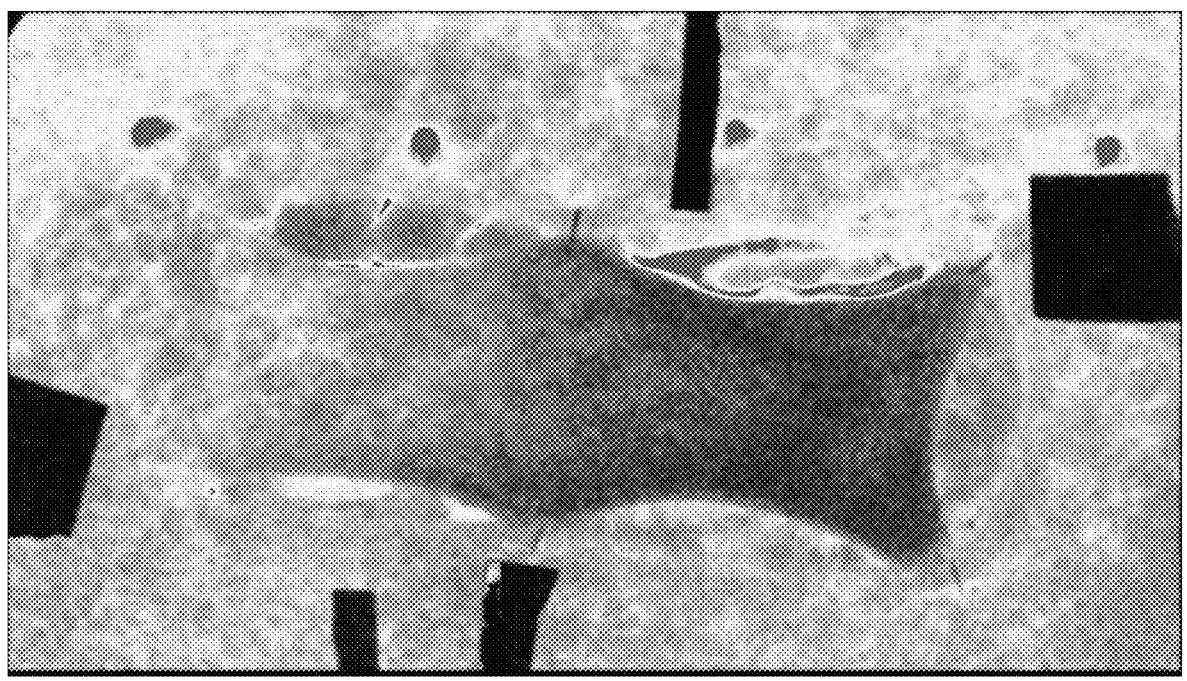
Figure 10A:
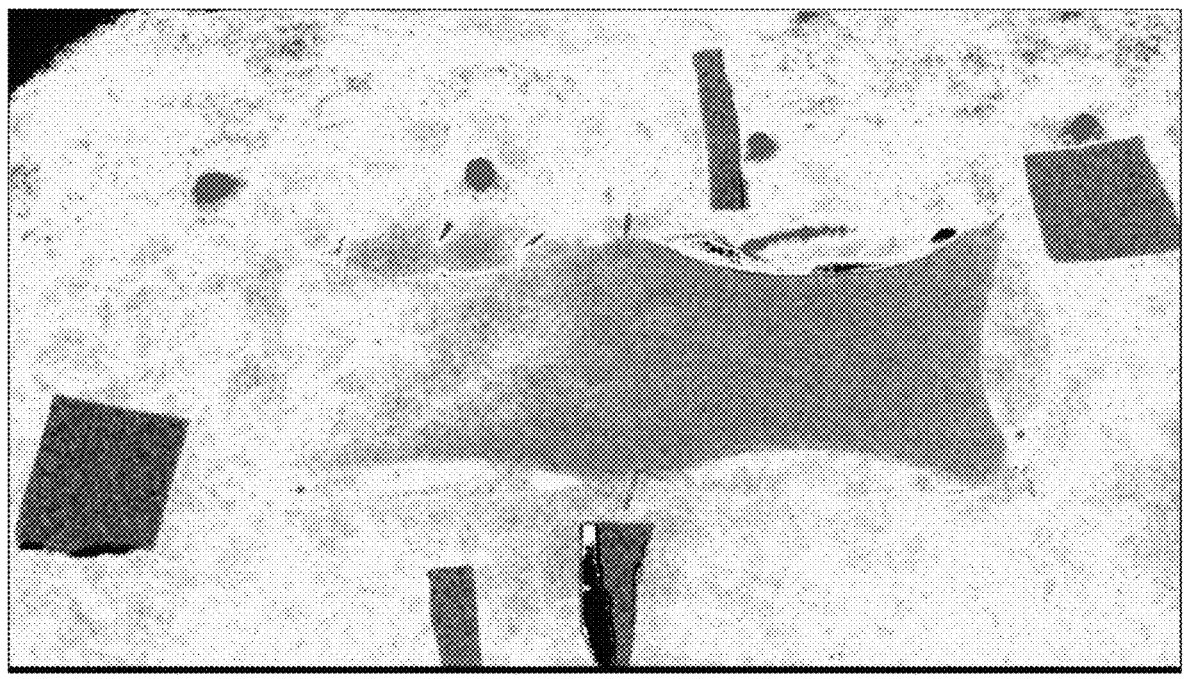
FIGS. 10A and 10B show sample uncorrected laser speckle images and images corrected for speckle motion artifact, respectively, obtained with the imaging device manually held in two hands.
Figure 10B:
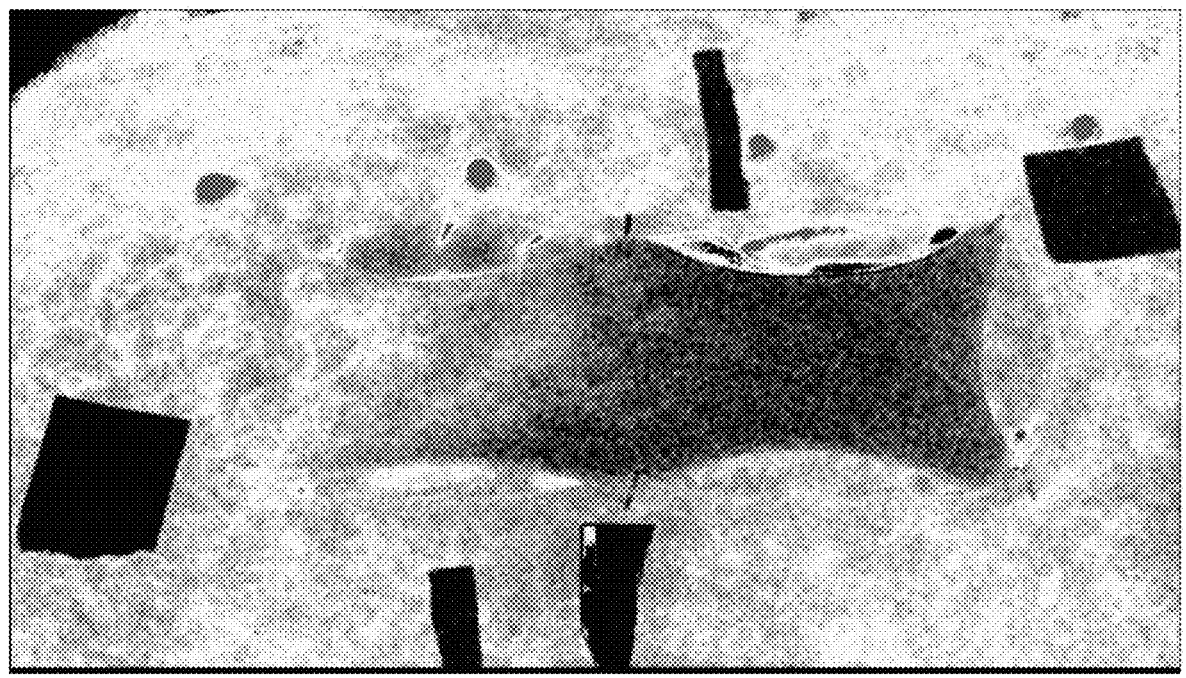
Figure 11A:
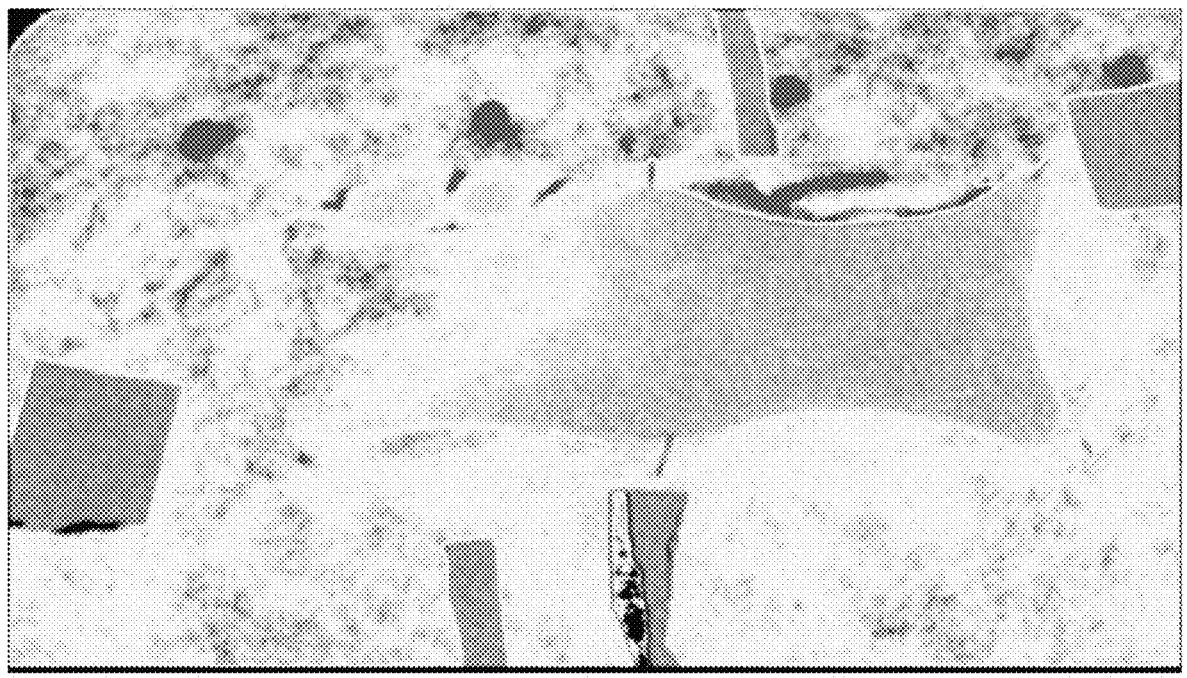
FIGS. 11A and 11B show sample uncorrected laser speckle images and images corrected for speckle motion artifact, respectively, obtained with the imaging device manually held in one hand.
Figure 11B:
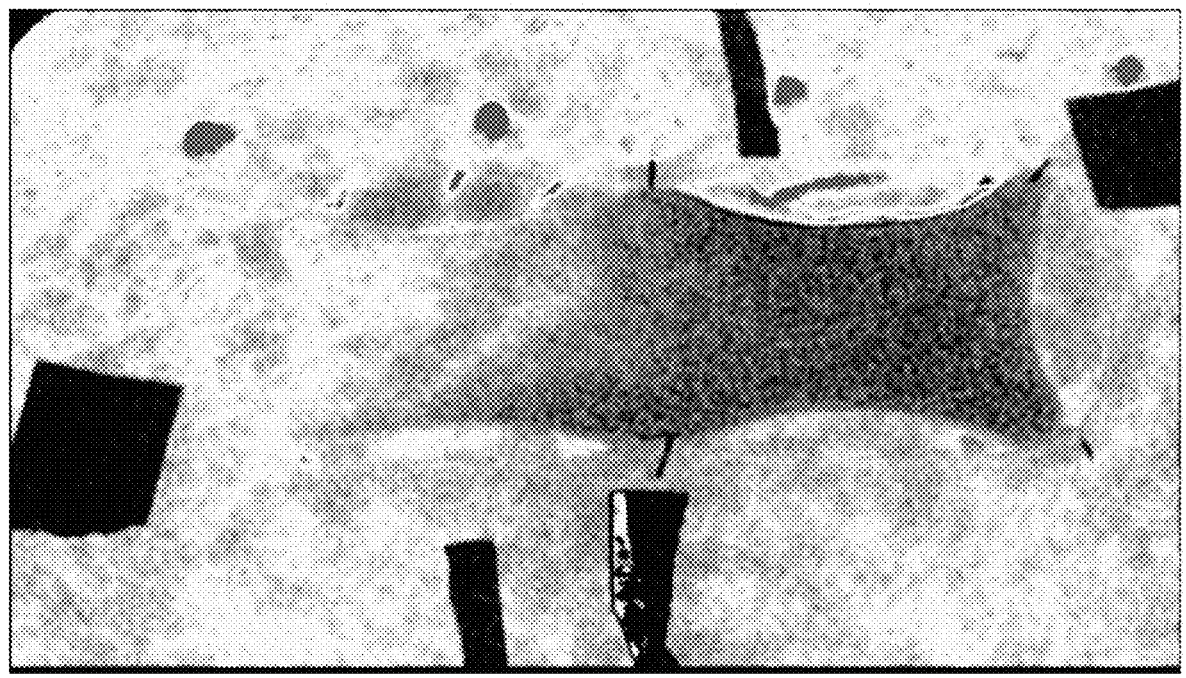
Figure 12A:
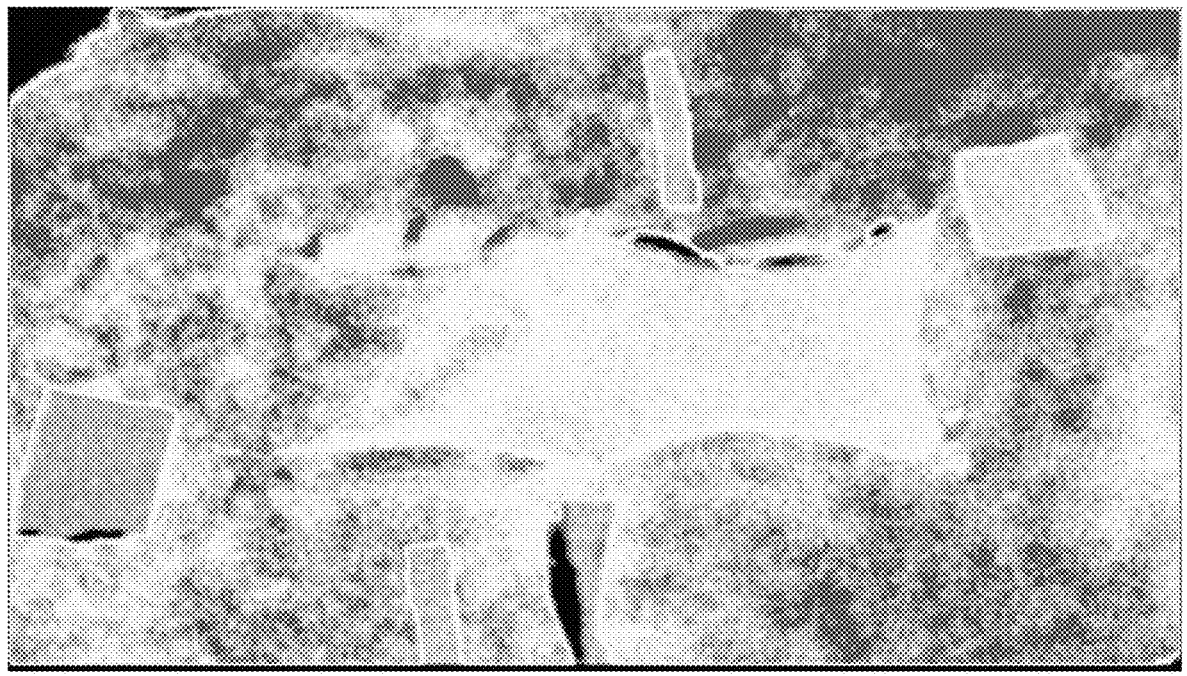
FIGS. 12A and 12B show sample uncorrected laser speckle images and images corrected for speckle motion artifact, respectively, obtained with the imaging device manually held and while translating the device along the imaging optical axis.
Figure 12B:
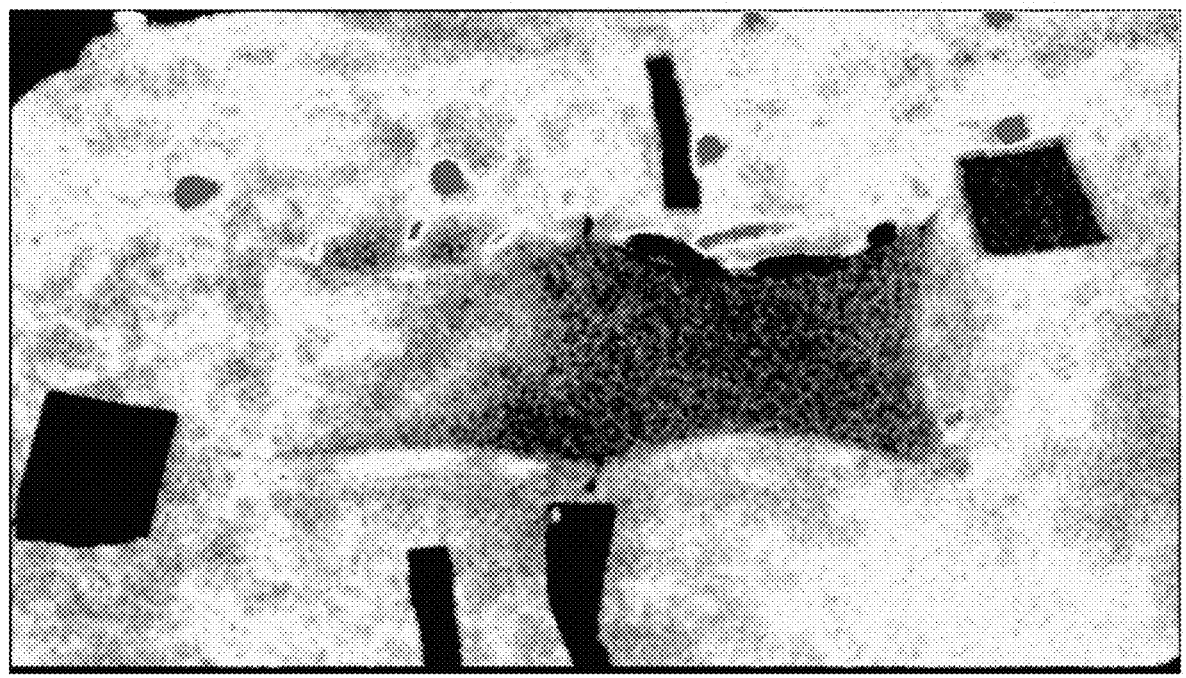
Figure 13A:
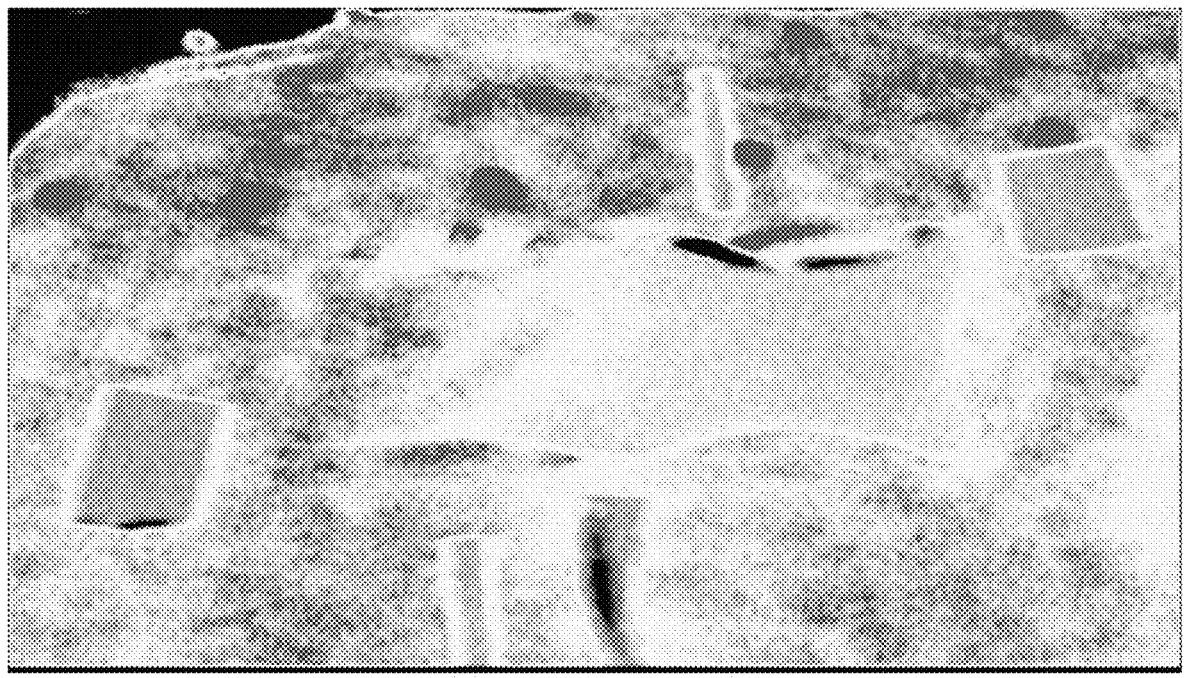
FIGS. 13A and 13B show sample uncorrected laser speckle images and images corrected for speckle motion artifact, respectively, obtained with the imaging device manually held and while translating the device perpendicular to the imaging optical axis.
Figure 13B:
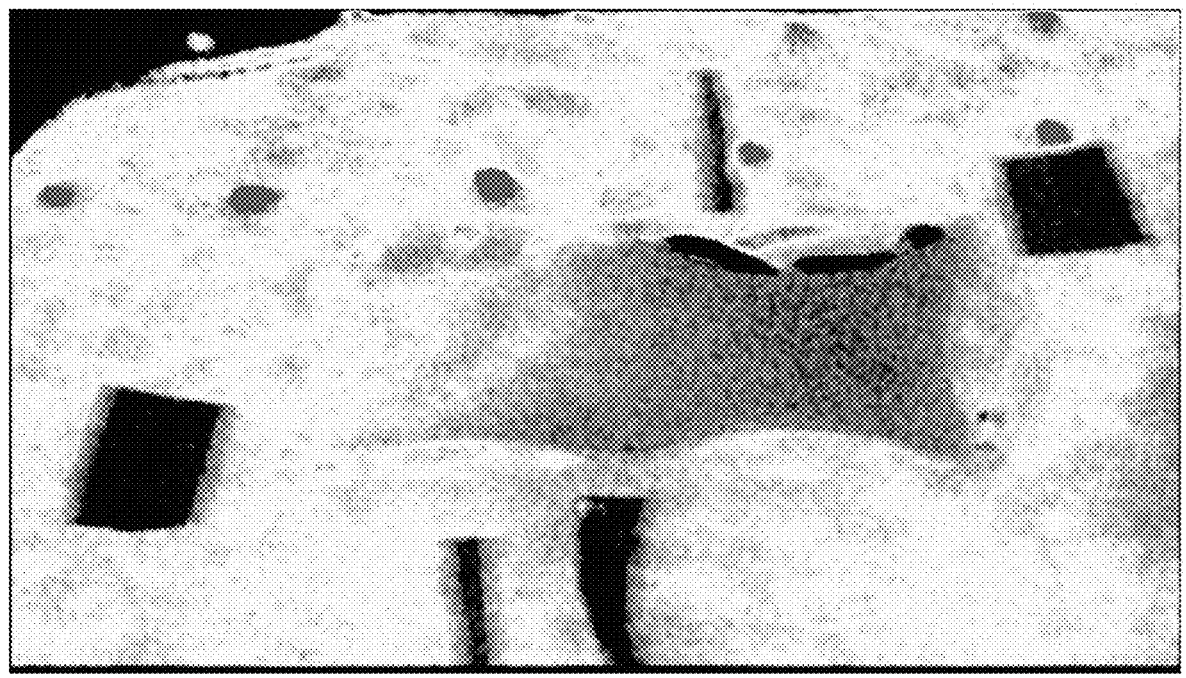
Figure 14A:
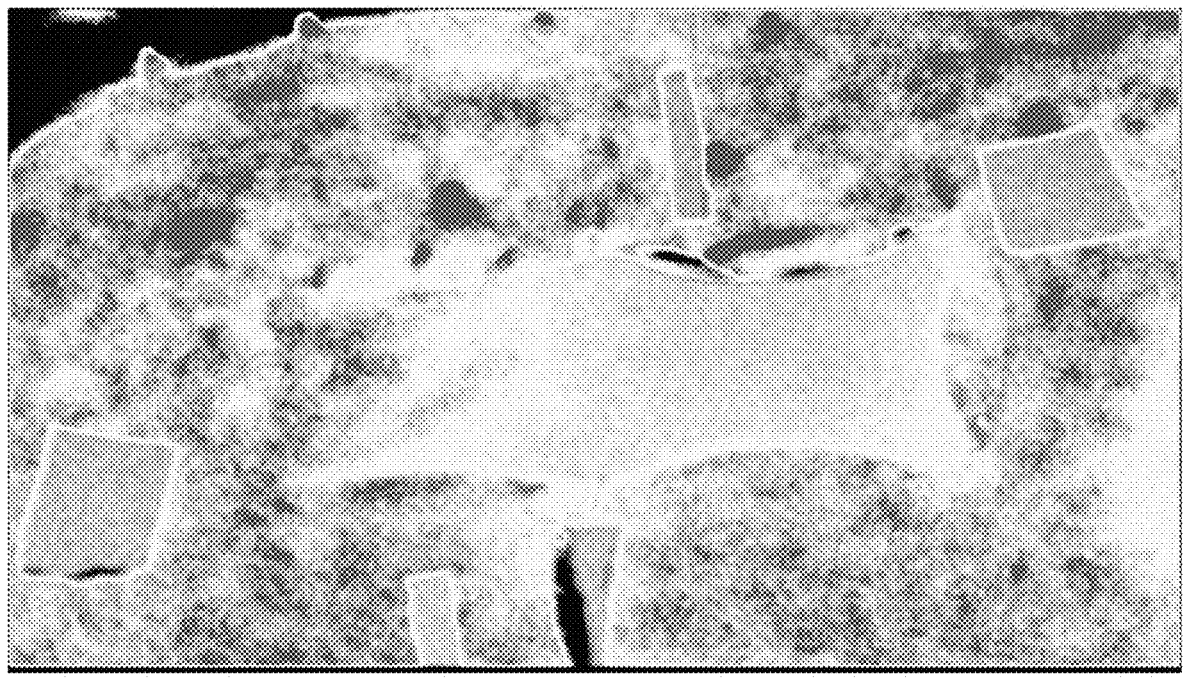
FIGS. 14A and 14B show sample uncorrected laser speckle images and images corrected for speckle motion artifact, respectively, obtained with the imaging device manually held and while rotating the device about the imaging optical axis.
Figure 14B:
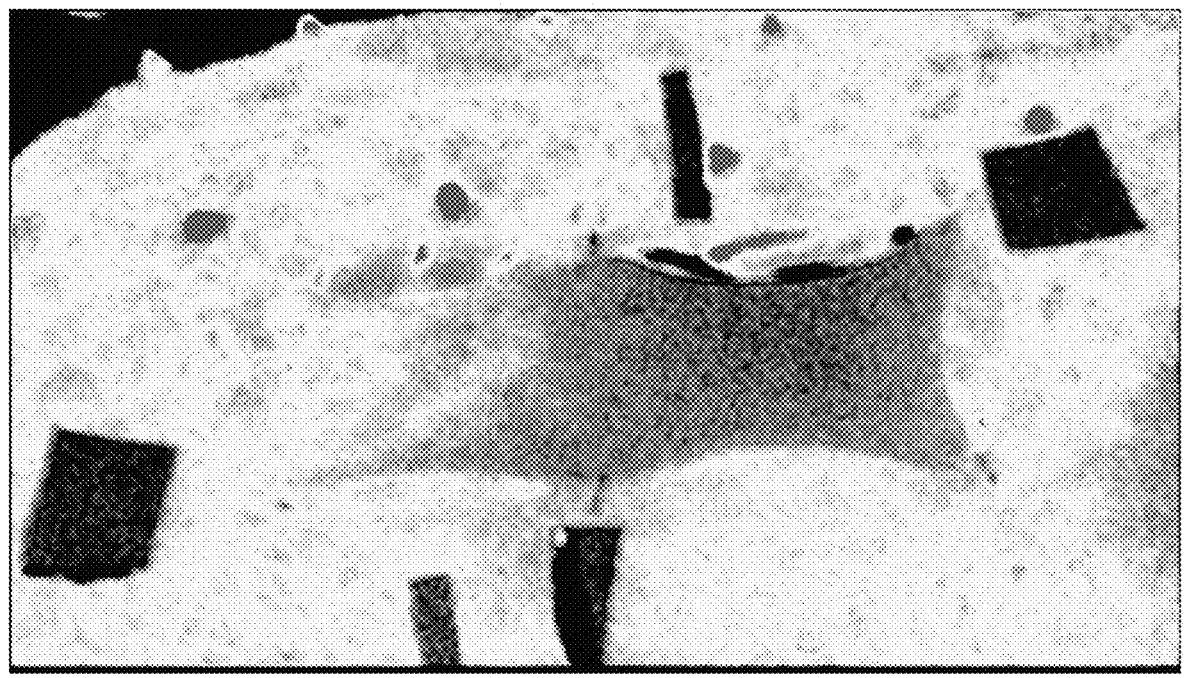

Several figures (FIGS. 9A to 14B) showing exemplary laser speckle images without and with subject-devicespeckle motion artifact correction are described below. The images in these figures were obtained from laser speckle imaging of a porcine model of decreased skin perfusion after a skin flap (10 cm by 6 cm, centered in images) was created in the groin region. Two adhesive patches for motion detection (seen at left and right edges of images), similar to patch 300 described above, were placed near the skin flap region. Motion correction was performed by subtracting the laser speckle image signal obtained over the patches from the overall laser speckle image signal. Figures are shown in sets including an uncorrected image figure A followed by a speckle motion artifact corrected image figure B. The color map images map relative perfusion values to a scale from blue (low) to white to yellow to red (high). Figures are shown and described for various scenarios that may affect the motion between the imaging device and the subject, including fixed mounting of the device (FIGS. 9A-9B), manually attempting to hold the device still in two hands (FIGS. 10A-10B), manually attempting to hold the device still in one hand (FIGS. 11A-11B), holding the device in one hand and slowly translating the device along the imaging optical axis toward and away from the subject (FIGS. 12A-12B), holding the device in one hand and slowly translating the device perpendicular to the optical axis from side to side (FIGS. 13A-13B), and holding the device in one hand and slowly rotating the device about the optical axis (FIGS. 14A-14B).

Comparison of the uncorrected image (FIG. 9A) and speckle motion artifact corrected image (FIG. 9B) taken with the imaging device mounted in a fixed position shows very little difference between the two image sets, as would be expected since there is minimal motion between the device and subject in this scenario. Some subject-device motion may still occur in such a scenario, however, for example due to subject tissue motion related to respiratory or circulatory functions, and a slight reduction in the displayed perfusion values is seen in the speckle motion artifact corrected images. Attempting to hold the laser speckle imaging device still in both hands is expected to yield the least amount of subject-device motion among the handheld device scenarios. Comparison of the uncorrected image (FIG. 10A) and speckle motion artifact corrected image (FIG. 10B) in this scenario shows a noticeable reduction in the displayed perfusion values for the speckle motion artifact corrected images, bringing the values to similar levels as the images from the fixed mounted device.

Attempting to hold the laser speckle imaging device still in one hand is expected to yield somewhat more subject-device motion compared to holding still with two hands. Comparison of the uncorrected image (FIG. 11A) and speckle motion artifact corrected image (FIG. 11B) in this one-handed scenario shows a substantial reduction in the displayed perfusion values in the speckle motion artifact corrected images, with that correction yielding much more discernable perfusion details (eg. the white regions seen in FIG. 11B) in the tissue in and around the skin flap.

The three handheld device scenarios with slow device motion introduced are intended to yield more subject-device motion compared to the other conditions, in order to assess how a motion correction method with use of a patch may perform in the presence of such device operator hand motions. Comparison of the uncorrected image (FIG. 12A) and speckle motion artifact corrected image (FIG. 12B) acquired when translating the device along the optical axis shows a very substantial reduction in the displayed perfusion values, yielding a similar level of detail in perfusion pattern as for the mounted/fixed and relatively still handheld scenarios. Comparison of the uncorrected images (FIG. 13A and FIG. 14A) and speckle motion artifact corrected images (FIG. 13B and FIG. 14B) acquired when translating the device perpendicular to the optical axis, and when rotating the device about the optical axis, respectively, showed very substantial reductions in the displayed perfusion values, yielding improved detail in the perfusion patterns visible.

Figure 15A:
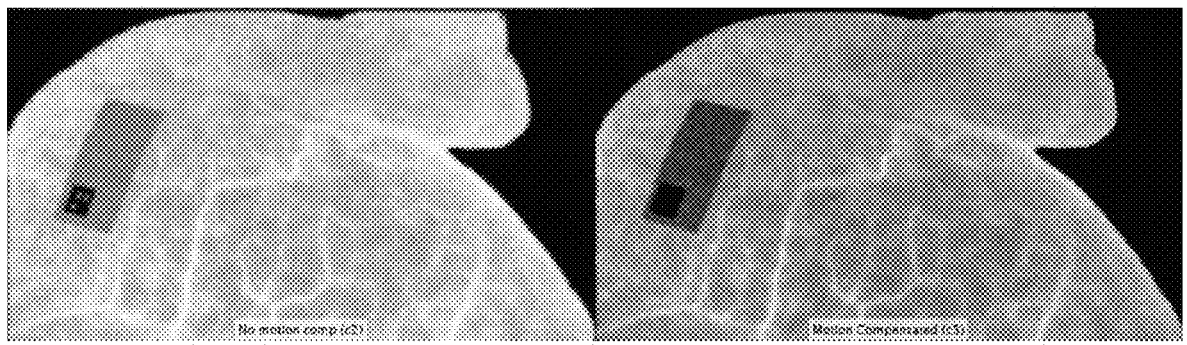
FIGS. 15A-15C show sample uncorrected laser speckle images (left) and images corrected for speckle motion artifact (right) obtained at various levels of camera motion increasing from 15A to 15C.
Figure 15B:
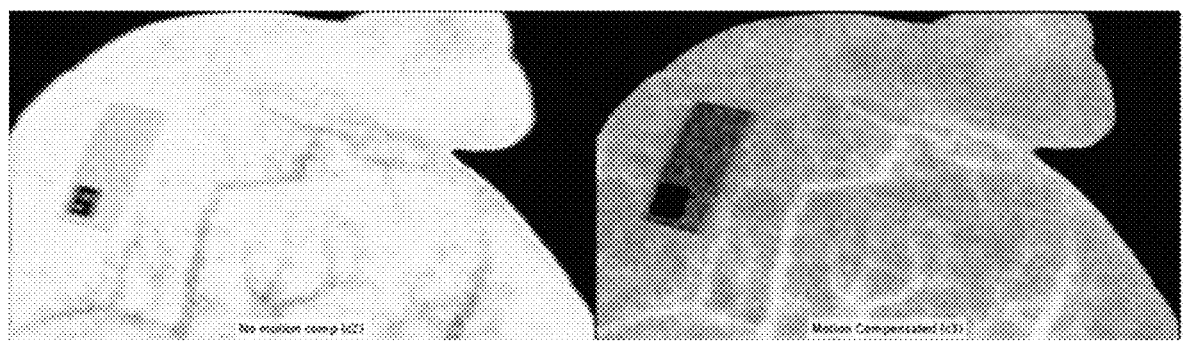
Figure 15C:
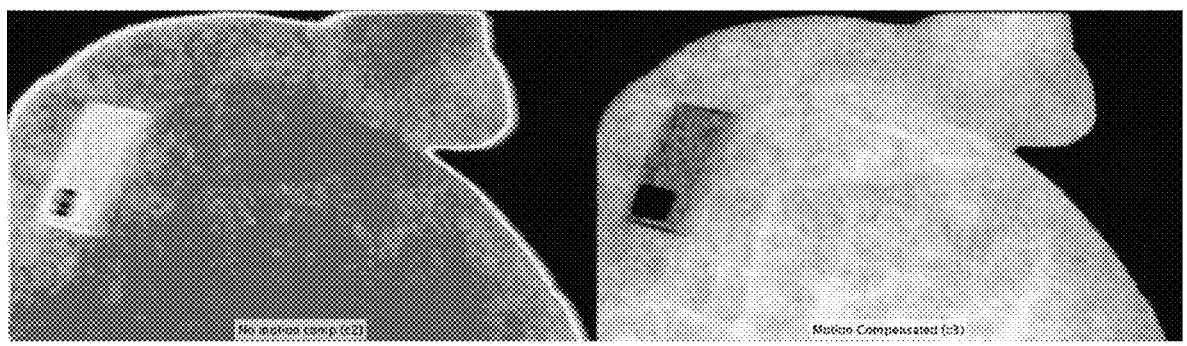

FIGS. 15A-C show exemplary images of base perfusion in the porcine model groin at varying amounts of subject-device motion, with the images corrected for speckle motion artifact (right) seen to more reliably depict the baseline perfusion and associated vasculature as compared to the uncorrected images (left).

Figure 16A:
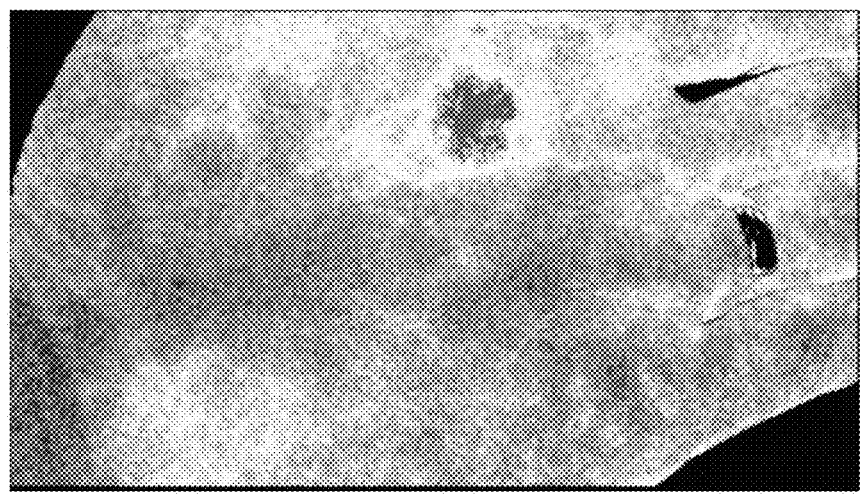
FIG. 16A shows a typical laser speckle image acquired while the camera was handheld in a relatively stable position.
Figure 16B:
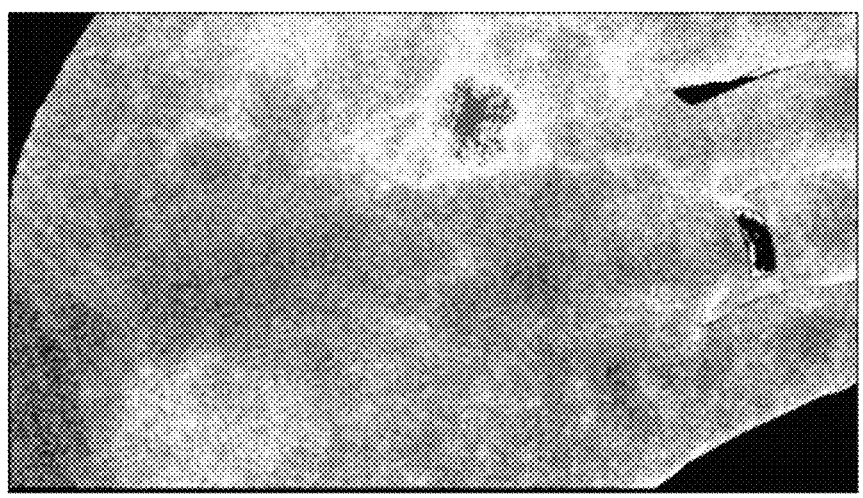
FIG. 16B shows an automatically chosen candidate image from within the nearby set of acquired images of that of the image of FIG. 16A.
Figure 16C:
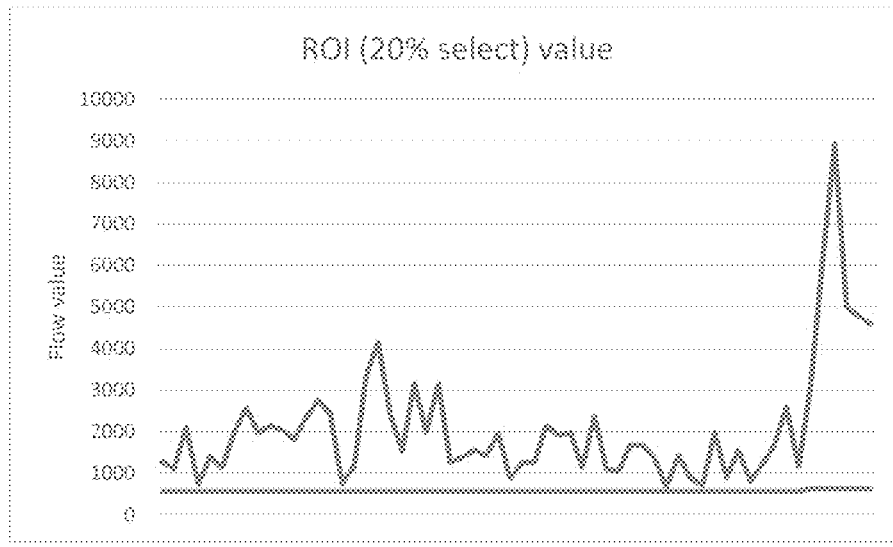
FIG. 16C shows an average measured LSI value from within a region of interest (ROI) over the set of acquired images of FIG. 16B.
Figure 17A:
FIG. 17A shows a typical laser speckle image acquired while the camera was handheld with significant camera motion.
Figure 17B:
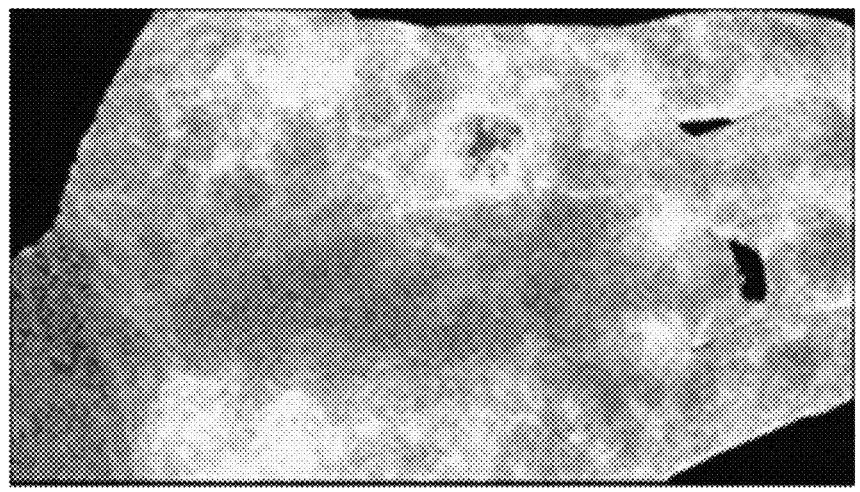
FIG. 17B shows an automatically chosen candidate image from within the nearby set of acquired images of that of the image of FIG. 17A.
Figure 17C:
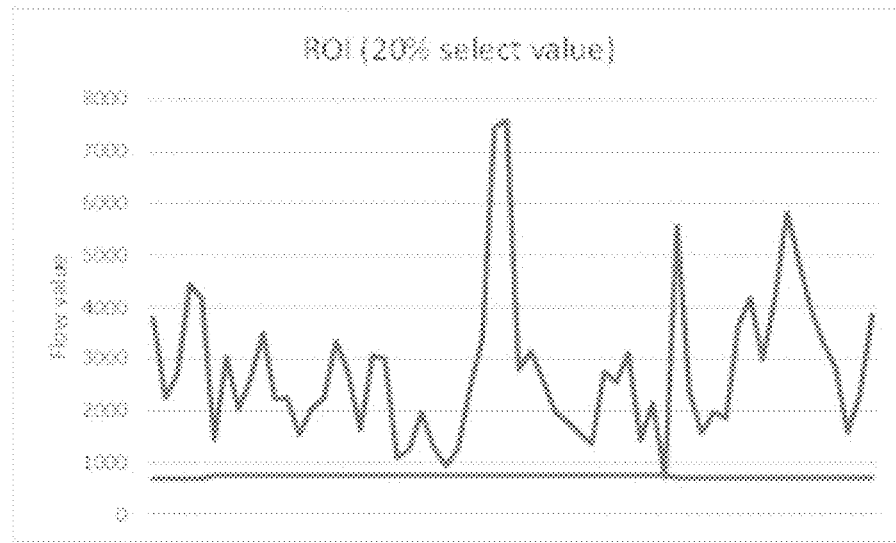
FIG. 17C shows an average measured LSI value from within a region of interest (ROI) over the set of acquired images of FIG. 17B.

FIGS. 16A-17C demonstrate the use of a method as described herein according to an embodiment to automatically choose a candidate image that minimizes the speckle motion artifact from within a set of images acquired within a period. FIG. 16A shows a typical image acquired while the camera was handheld in a relatively stable position, FIG. 16B shows an automatically chosen candidate image from within the nearby set of acquired images, and FIG. 16C shows an average measured LSI value from within a region of interest (ROI) over the set of acquired images. The red line in FIG. 16C shows the minimum value of the ROI average LSI value from nearby acquired images, which is used to automatically select the candidate image. In this example case of stable camera and subject position, there is no noticeable difference between the typical and automatically chosen candidate image. FIG. 17A shows a typical image acquired while the camera was handheld with significant camera motion, FIG. 17B shows an automatically chosen candidate image from within the nearby set of acquired images, and FIG. 17C shows an average measured perfusion value from within a region of interest (ROI) over the set of acquired images. In this example case with significant camera motion there is a marked improvement seen from using the automatically chosen candidate image method.

Figure 18A:
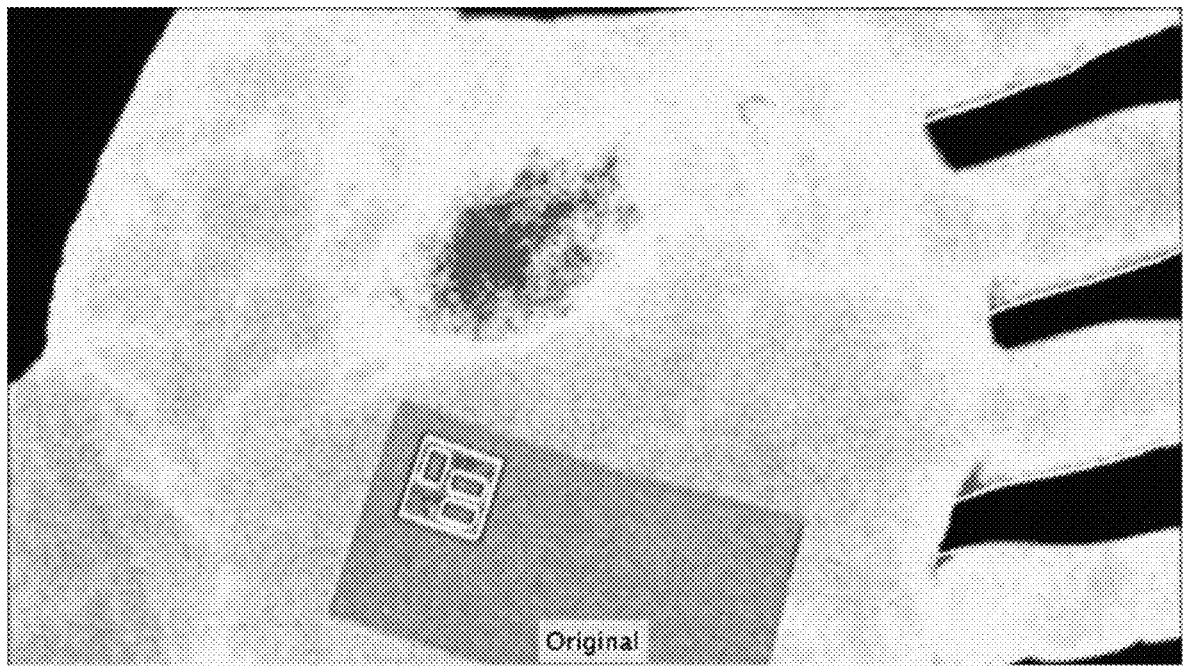
FIGS. 18A and 18B show sample laser speckle images acquired with no correction for speckle motion artifact under conditions of stable handheld camera and moving handheld camera, respectively.
Figure 18B:
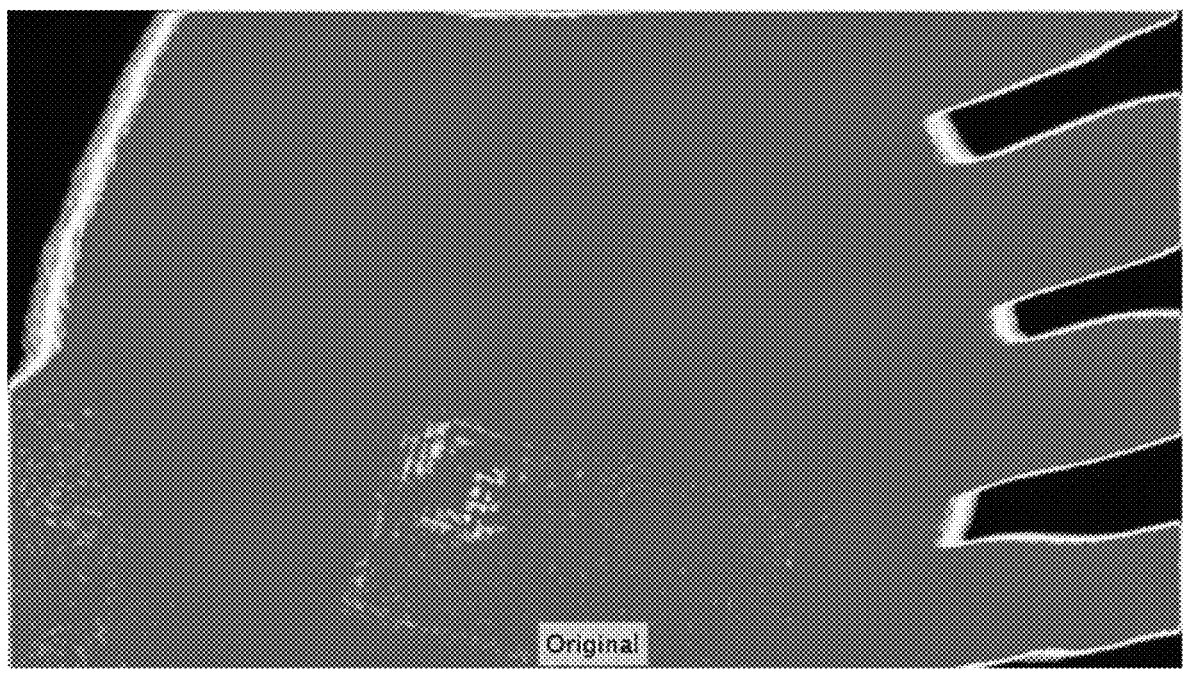

FIGS. 18A-20B show sample images demonstrating the benefit of speckle motion artifact correction using both offset and scaling corrections according to methods as described herein. FIGS. 18A and 18B show sample laser speckle images acquired with no correction for speckle motion artifact under conditions of stable handheld camera and moving handheld camera, respectively.

Figure 19A:
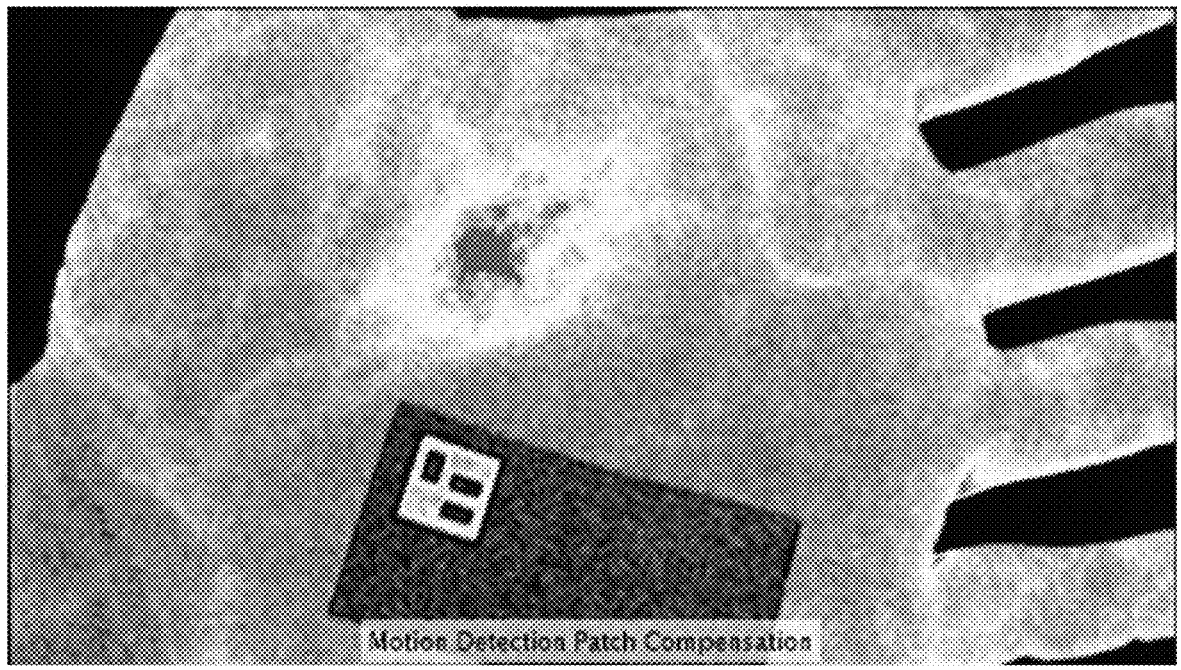
FIG. 19A shows a sample laser speckle image acquired with speckle motion artifact correction with offset applied under a stable handheld camera condition.
Figure 19B:
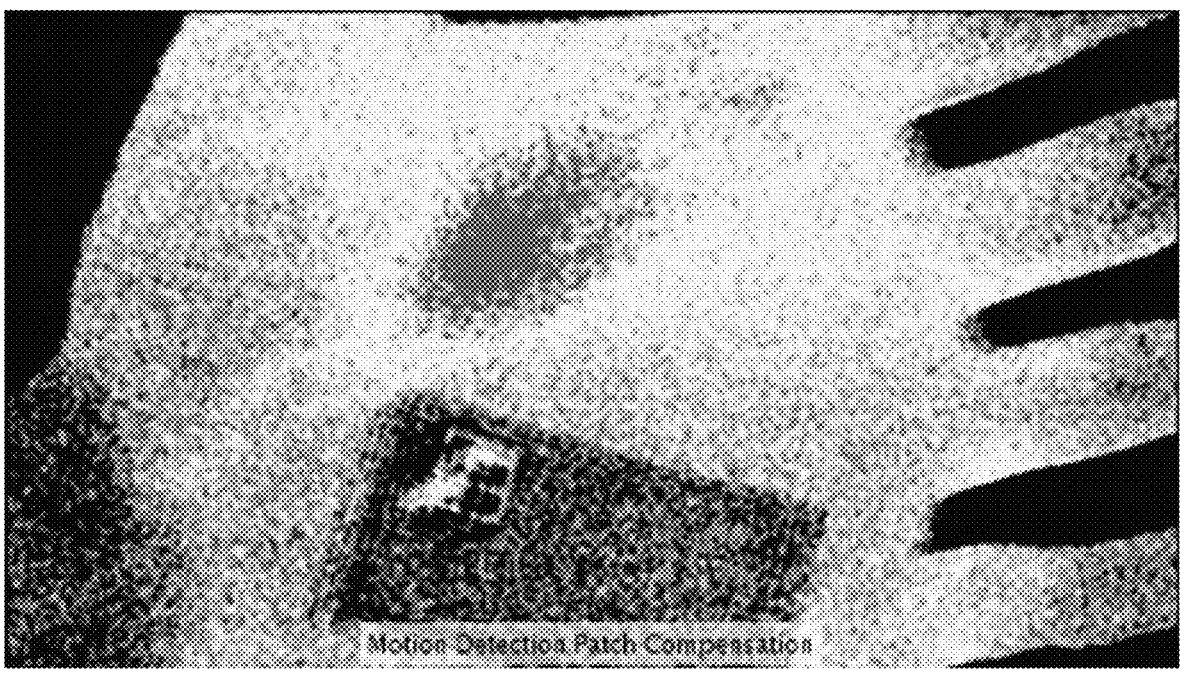
FIG. 19B shows a sample laser speckle image acquired with speckle motion artifact correction with offset applied under a moving handheld camera condition.

FIG. 19A shows a sample laser speckle image acquired with speckle motion artifact correction with offset applied under a stable handheld camera condition, while FIG. 19B shows a similar image acquired under a moving handheld camera condition. The offset was determined based on the value measured at the speckle target region of the motion detection patch. As can be seen in the example images, while correction of speckle motion artifact with an offset value model (FIG. 19B) dramatically improves the image during the moving camera condition it appears to show an increased region of high perfusion (shown in red) as compared to the image obtained in the stable handheld camera condition (FIG. 19A).

Figure 20A:
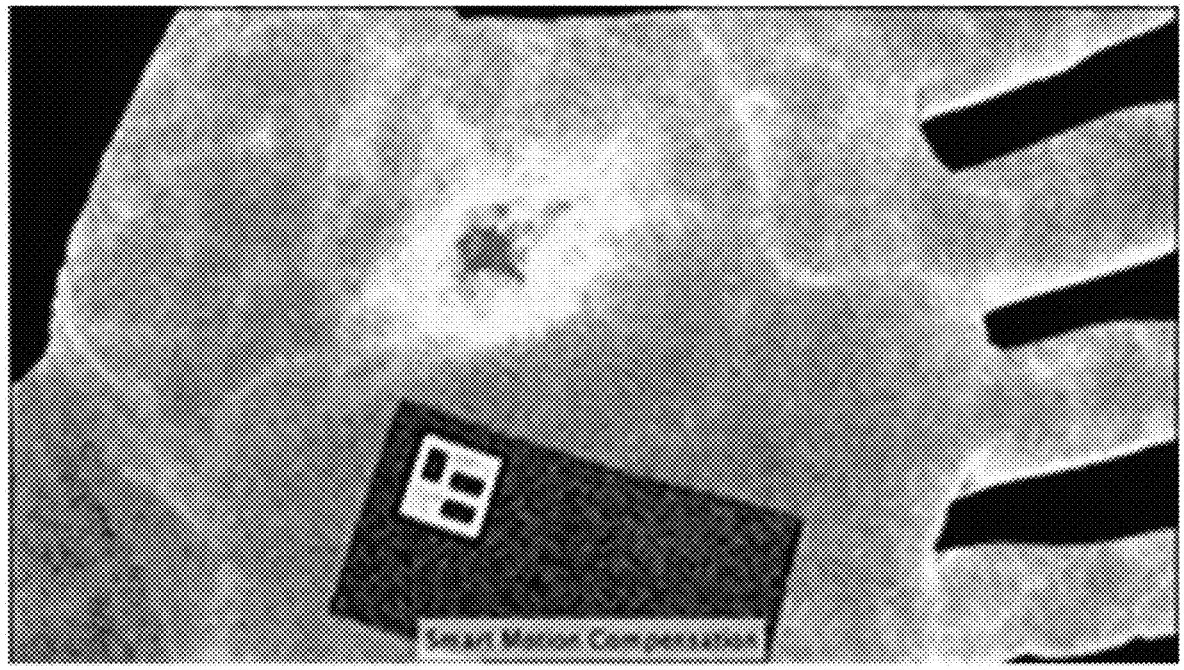
FIG. 20A shows a sample laser speckle image acquired with speckle motion artifact correction with offset and scaling applied under a stable handheld camera condition.
Figure 20B:
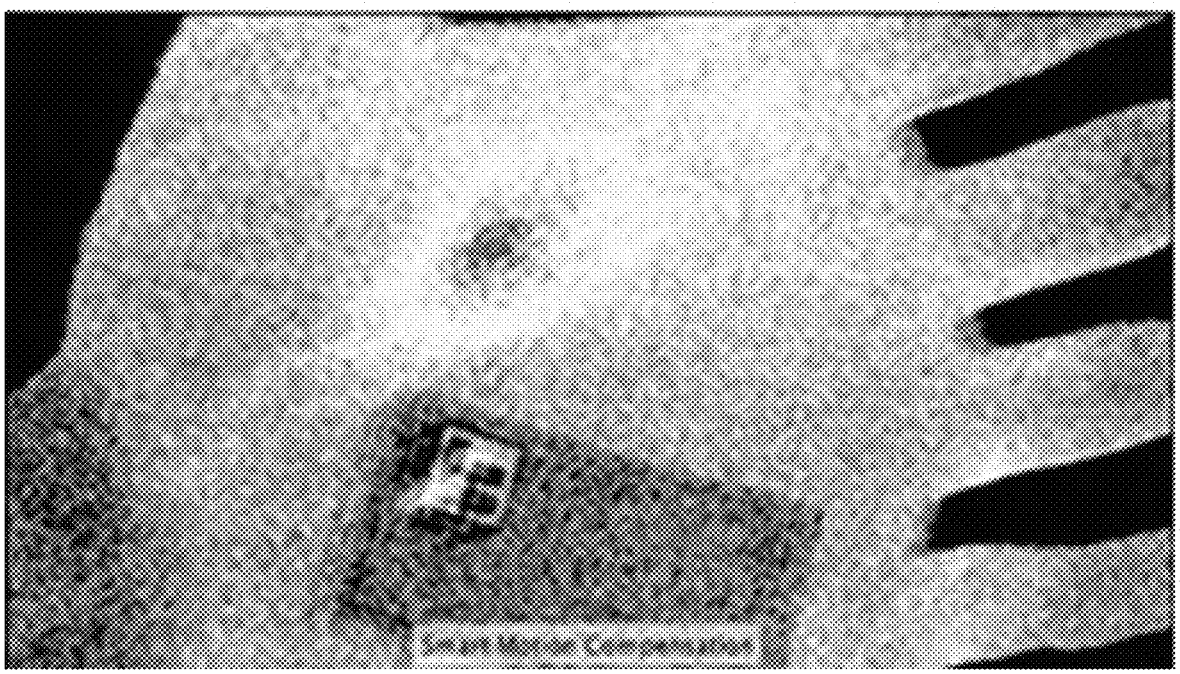
FIG. 20B shows a sample laser speckle image acquired with speckle motion artifact correction with offset and scaling applied under a moving handheld camera condition.

FIG. 20A shows a sample laser speckle image acquired with speckle motion artifact correction with offset and scaling applied under a stable handheld camera condition while FIG. 20B shows a similar image acquired under a moving handheld camera condition. The scaling and offset were determined using the minimum measure of relative subject-device motion method. By correcting the speckle motion artifact with both an offset and scaling model the region of high perfusion (shown in red) obtained under the camera motion condition (FIG. 20B) may be seen to compare more closely with the corresponding region of high perfusion obtained under the stable handheld camera condition.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments; however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:
1. A method for compensating for speckle motion artifacts in medical laser speckle imaging of a target tissue area, comprising:
    providing a series of laser speckle images of the target tissue area, the series of images acquired by a laser speckle imaging device;

calculating a measure of relative motion between a first image in the series and a second image in the series;

calculating a scaling factor and an offset value based on the calculated measure of relative motion, wherein the offset value is further calculated based on the scaling factor; and correcting image data of the second image to compensate for speckle motion artifacts by applying the scaling factor and the offset value to the image data.

2. The method of claim 1, wherein the series of images includes at least 30 images.

3. The method of claim 1, wherein the series of images is acquired during a continuous period of time.

4. The method of claim 3, wherein the continuous period of time comprises at least 2 seconds.

5. The method of claim 1, wherein calculating the measure of relative motion is based on a measured image signal from a device attached to tissue in the target tissue area.

6. The method of claim 1, wherein calculating the measure of relative motion is based on measurements by a motion sensor mounted to the laser speckle imaging device, the measurements having been acquired simultaneously with the acquisition of the series of images.

7. The method of claim 1, wherein calculating the measure of relative motion is based on calculating, for each image in the series of laser speckle images, a representative value for the laser speckle image signal within a region of interest.

8. The method of claim 7, wherein calculating the measure of relative motion comprises:

determining a minimum representative value among the representative values for all images in the series of laser speckle images; and calculating a difference between the representative value for each image in the series of laser speckle images and the minimum representative value;

wherein the measure of relative motion for each image in the series of laser speckle images is based on the calculated difference for that image.

9. The method of claim 7, wherein the region of interest comprises about one quarter of the total number of pixels in each image in the series of laser speckle images, and includes pixels at the center of each image and excludes pixels at the edges of each image.

10. The method of claim 7, wherein each representative value is a mean value of pixel signal values within the respective region of interest.

11. The method of claim 7, wherein each representative value is a percentile value of pixel signal values within the respective region of interest.

12. The method of claim 7, wherein each representative value is the $20^{th}$ percentile value of pixel signal values within the respective region of interest.

13. The method of claim 7, wherein pixel signal values below a first threshold value are excluded from the calculation of each representative value.

14. The method of claim 7, wherein pixel signal values above a second threshold value are excluded from the calculation of each representative value.

15. The method of claim 1, wherein calculating the measure of relative motion is based on calculating, for each image in the series of laser speckle images, a first representative value for the laser speckle image signal within a first region of interest and a second representative value within a second region of interest.

16. The method of claim 15, wherein calculating the measure of relative motion comprises:

determining a minimum first representative value among the first representative values for all images in the series of laser speckle images;

calculating a first difference between the first representative value for each image in the series of laser speckle images and the minimum first representative value;

determining a minimum second representative value among the second representative values for all images in the series of laser speckle images; and calculating a second difference between the second representative value for each image in the series of laser speckle images and the minimum second representative value;

wherein the measure of relative motion for each image in the series of laser speckle images is based on the calculated first and second differences for an image.

17. The method of claim 16, wherein calculating the measure of relative motion further comprises:

calculating an intermediate representative value in an intermediate region of interest between the first and second regions of interest, wherein the intermediate representative value is interpolated based on the first and second representative values;

determining a minimum intermediate representative value among the intermediate representative values for all images in the series of laser speckle images; and calculating a third difference between the intermediate representative value for each image in the series of laser speckle images and the minimum intermediate representative value.

18. The method of claim 1, further comprising acquiring a second series of laser speckle images of the target tissue area, the second series of images acquired by the laser speckle imaging device subsequently to acquisition of the first and second images, wherein correcting the image data of the second image is performed while acquiring the second series of images.

19. The method of claim 1, wherein the scaling factor and the offset value used for correcting the image data of the second image to compensate for speckle motion artifacts satisfy the following equations:

$$SF=1/(1+A \times i)$$

and $$O=SF \times (B \times i+C)$$

wherein SF is the scaling factor, A is a first calibration constant, i is the measure of relative motion for the second image, O is the offset, B is a second calibration constant, and C is a third calibration constant.

20. The method of claim 1, wherein the scaling factor is calculated based on a first calibration constant and the calculated measure of relative motion.

21. The method of claim 20, wherein the offset value is calculated based on the calculated measure of relative motion and a plurality of calibration constants that includes the first calibration constant.

22. A system for compensating for speckle motion artifacts in medical laser speckle imaging of a target tissue area, comprising one or more processors, memory, and one or more programs stored in the memory and comprising instructions for execution by the one or more processors for:

receiving a series of laser speckle images of the target tissue area, the series of images acquired by a laser speckle imaging device;

calculating a measure of relative motion between a first image in the series and a second image in the series;

calculating a scaling factor and an offset value based on the calculated measure of relative motion, wherein the offset value is further calculated based on the scaling factor; and correcting image data of the second image to compensate for speckle motion artifacts by applying the scaling factor and the offset value to the image data.

23. The system of claim 22, wherein the series of images includes at least 30 images.

24. The system of claim 22, wherein the series of images is acquired during a continuous period of time.

25. The system of claim 24, wherein the continuous period of time comprises at least 2 seconds.

26. The system of claim 22, wherein calculating the measure of relative motion is based on a measured image signal from a device attached to tissue in the target tissue area.

27. The system of claim 22, wherein calculating the measure of relative motion is based on measurements by a motion sensor mounted to the laser speckle imaging device, the measurements having been acquired simultaneously with the acquisition of the series of images.

28. The system of claim 22, wherein calculating the measure of relative motion is based on calculating, for each image in the series of laser speckle images, a representative value for the laser speckle image signal within a region of interest.

29. The system of claim 28, wherein calculating the measure of relative motion comprises:

determining a minimum representative value among the representative values for all images in the series of laser speckle images; and calculating a difference between the representative value for each image in the series of laser speckle images and the minimum representative value;

wherein the measure of relative motion for each image in the series of laser speckle images is based on the calculated difference for that image.

30. The system of claim 28, wherein the region of interest comprises about one quarter of the total number of pixels in each image in the series of laser speckle images, and includes pixels at the center of each image and excludes pixels at the edges of each image.

31. The system of claim 28, wherein each representative value is a mean value of pixel signal values within the respective region of interest.

32. The system of claim 28, wherein each representative value is a percentile value of pixel signal values within the respective region of interest.

33. The system of claim 28, wherein each representative value is the $20^{th}$ percentile value of pixel signal values within the respective region of interest.

34. The system of claim 28, wherein pixel signal values below a first threshold value are excluded from the calculation of each representative value.

35. The system of claim 28, wherein pixel signal values above a second threshold value are excluded from the calculation of each representative value.

36. The system of claim 22, wherein calculating the measure of relative motion is based on calculating, for each image in the series of laser speckle images, a first representative value for the laser speckle image signal within a first region of interest and a second representative value within a second region of interest.

37. The system of claim 36, wherein calculating the measure of relative motion comprises:

determining a minimum first representative value among the first representative values for all images in the series of laser speckle images;

calculating a first difference between the first representative value for each image in the series of laser speckle images and the minimum first representative value;

determining a minimum second representative value among the second representative values for all images in the series of laser speckle images; and calculating a second difference between the second representative value for each image in the series of laser speckle images and the minimum second representative value;

wherein the measure of relative motion for each image in the series of laser speckle images is based on the calculated first and second differences for an image.

38. The system of claim 37, wherein calculating the measure of relative motion further comprises:

calculating an intermediate representative value in an intermediate region of interest between the first and second regions of interest, wherein the intermediate representative value is interpolated based on the first and second representative values;

determining a minimum intermediate representative value among the intermediate representative values for all images in the series of laser speckle images; and calculating a third difference between the intermediate representative value for each image in the series of laser speckle images and the minimum intermediate representative value.

39. The system of claim 22, wherein the one or more programs further comprise instructions for acquiring a second series of laser speckle images of the target tissue area, the second series of images acquired by the laser speckle imaging device subsequently to acquisition of the first and second images, wherein correcting the image data of the second image is performed while acquiring the second series of images.

40. The system of claim 22, wherein the scaling factor and the offset value used for correcting the image data of the second image to compensate for speckle motion artifacts satisfy the following equations:

$$SF=1/(1+A\times i)$$

and $$O=SF\times(B\times i+C)$$

wherein SF is the scaling factor, A is a first calibration constant, i is the measure of relative motion for the second image, O is the offset, B is a second calibration constant, and C is a third calibration constant.

* * * * *